US012807976B2

(12) United States Patent
Wu et al.

(10) Patent No.: US 12,807,976 B2
(45) Date of Patent: Nov. 24, 2026

(54) GENETICALLY ENGINEERED BACTERIUM AND A PREPARATION METHOD AND USE THEREOF

(71) Applicant: SYNAURA BIOTECHNOLOGY (SHANGHAI) CO., LTD., Shanghai (CN)

(72) Inventors: Yan Wu, Shanghai (CN); Jing Tang, Shanghai (CN); Jin Zhao, Shanghai (CN); Shu Wang, Shanghai (CN); Zhenhua Tian, Shanghai (CN); Fei Yao, Shanghai (CN); Miao Li, Shanghai (CN); Hong Xu, Shanghai (CN); Chenxi Huang, Shanghai (CN); Yurou Liu, Shanghai (CN)

(73) Assignee: SYNAURA BIOTECHNOLOGY (SHANGHAI) CO., LTD., Shanghai (CN)

( * ) Notice: Subject to any disclaimer, the term of this patent is extended or adjusted under 35 U.S.C. 154(b) by 92 days.

(21) Appl. No.: 18/576,607

(22) PCT Filed: Oct. 12, 2022

(86) PCT No.: PCT/CN2022/124826

§ 371 (c)(1),
(2) Date: Jan. 4, 2024

(87) PCT Pub. No.: WO2023/103578

PCT Pub. Date: Jun. 15, 2023

(65) Prior Publication Data

US 2024/0318214 A1 Sep. 26, 2024

(30) Foreign Application Priority Data

Dec. 10, 2021 (CN) ......................... 202111509981.9

(51) Int. Cl.

| | |
|---|---|
| ***C12P 19/04*** | (2006.01) |
| ***C12N 1/20*** | (2026.01) |
| ***C12N 9/10*** | (2006.01) |
| ***C12N 15/70*** | (2006.01) |
| ***C12P 19/18*** | (2006.01) |
| ***C12R 1/19*** | (2006.01) |

(52) U.S. Cl.

CPC ................ *C12P 19/04* (2013.01); *C12N 1/20* (2013.01); *C12N 9/1051* (2013.01); *C12N 15/70* (2013.01); *C12P 19/18* (2013.01); *C07K 2319/24* (2013.01); *C07K 2319/35* (2013.01); *C12R 2001/19* (2021.05); *C12Y 204/01069* (2013.01)

(58) Field of Classification Search

None

See application file for complete search history.

(56) References Cited

U.S. PATENT DOCUMENTS

| | | | | |
|---|---|---|---|---|
| 2014/0274882 | A1* | 9/2014 | Kalkum | ............... G01N 33/573 435/23 |
| 2017/0152538 | A1 | 6/2017 | Lee et al. | |
| 2018/0265876 | A1 | 9/2018 | Yu et al. | |
| 2020/0181665 | A1 | 6/2020 | Jennewein et al. | |
| 2020/0338101 | A1 | 10/2020 | Kim et al. | |

FOREIGN PATENT DOCUMENTS

| | | | | |
|---|---|---|---|---|
| CN | 105874063 A | | 8/2016 | |
| CN | 108761076 A | | 11/2018 | |
| CN | 109890834 A | | 6/2019 | |
| CN | 111629732 A | | 9/2020 | |
| CN | 111808790 A | | 10/2020 | |
| CN | 112322565 A | * | 2/2021 | ........... C12N 9/1051 |
| CN | 112342176 A | | 2/2021 | |
| CN | 112501106 B | | 5/2021 | |
| CN | 110734889 B | | 7/2021 | |
| CN | 109402158 B | | 1/2022 | |
| CN | 114276971 A | | 4/2022 | |
| CN | 114480465 A | | 5/2022 | |
| CN | 114774343 A | | 7/2022 | |
| CN | 108473969 B | | 9/2022 | |
| CN | 115287273 A | | 11/2022 | |
| CN | 115786220 A | | 3/2023 | |
| CN | 116143936 A | * | 5/2023 | ....... C07K 14/43509 |

(Continued)

OTHER PUBLICATIONS

Uniprot, Accession No. A0A369HXL4, 2021, www.uniprot.org. (Year: 2021).*

(Continued)

*Primary Examiner* — Todd M Epstein

(74) *Attorney, Agent, or Firm* — Brooks Kushman P.C.

(57) ABSTRACT

A genetically engineered bacterium and a preparation method and use thereof are disclosed. The genetically engineered bacteria contain a gene encoding α-1,2-fucosyltransferase, and a gene encoding a protein tag is connected to the gene encoding α-1,2-fucosyltransferase; the protein tag is MBP, SUMO1, SUMO2 or TrxA, the amino acid sequence of the MBP is shown in SEQ ID NO: 2, the amino acid sequence of the SUMO1 is shown in SEQ ID NO: 3, the amino acid sequence of the SUMO2 is shown in SEQ ID NO: 4, the amino acid sequence of the TrxA is shown in SEQ ID NO: 5. Fermentation with the genetically engineered bacteria can greatly increase the yield of 2'-fucosyllactose compared to the genetically engineered bacteria that only expresses α-1,2-fucosyltransferase exogenously, and the yield can be more than doubled in a preferred case.

18 Claims, 3 Drawing Sheets

Specification includes a Sequence Listing.

(56) References Cited

FOREIGN PATENT DOCUMENTS

| | | | |
|---|---|---|---|
| CN | 112625990 | B | 6/2023 |
| CN | 113025548 | B | 6/2023 |
| CN | 116555145 | A | 8/2023 |
| CN | 116676243 | A | 9/2023 |
| EP | 3425052 | A1 | 1/2019 |
| EP | 3438122 | A1 | 2/2019 |
| WO | 2019104433 | A1 | 6/2019 |
| WO | 2023103578 | A1 | 6/2023 |

OTHER PUBLICATIONS

Uniprot, Accession No. A0A0F8NYV9, 2015, www.uniprot.org. (Year: 2015).*

International Search Report and Written Opinion or International Application No. PCT/CN2022/124826, dated Jan. 19, 2023 and Sep. 11, 2023 10 pages.

Lin Lu et al., Combinatorial Metabolic Engineering of *Escherichia coli* for De Novo Production of 2'-Fucosyllactose, Bioresource Technology, vol. 351 (2022) 126949, Mar. 4, 2022, XP087014275, ISSN: 0960-8524, DOI: 10.1016/J., Elsevier, Amsterdam, NL.

Ariyoshi, M., 等, Chain M, Maltodextrin-binding protein, Centromere protein N, Accession No. 7BXT_M, Feb. 12, 2021, Genbank Database.

Kegler,C.,SUMO3 [Cloning vectorpSUMO3_ck5], Accession No. AHY21933.1, May 4, 2014, Genbank Database.

Kolyadko,V.N.et al., Trx-Inf4-MutA[synthetic construct], Accession No. AHW 57454.1, Apr. 15, 2014, Genbank Database.

Zhai Y-F e al., "Research progress of human milk oligosaccharides synthesis in vitro," Science and Technology of Food Industry, V. 39. n. 5, with English Abstract, 2018, 5 pgs.

Chen, X. et al., "Research progress on human milk oligosaccharides (HMOs)" Fine and Specialty Chemicals, with English Abstract, Dec. 21, 2019, 3 pgs.

Shuhua, T., "Pharmaceutical Molecular Biology," China Pharmaceutical Science and Technology Press, p. 138, the SUMO Section (Aug. 30, 2017) and Machine Translation.

Sadr,V., 等,sumo-hepcidin [synthetic construct], Accession No. AQS95516.1, Feb. 27, 2017, Genbank Database.

Wang, G. ,alpha-1,2-fucosyltransferase [*Helicobacter pylori*], Accession No. AAC99764.1, Mar. 12, 1999, Genbank Database.

Office Action dated Feb. 8, 2024 for Chinese Appn. No. 202111509981.9, 23 pgs.

Int'l Preliminary Report on Patentability dated Dec. 3, 2024 for PCT Appn. No. PCT/CN2022/124826 filed Oct. 12, 2022, 15 pgs.

* cited by examiner

Fig. 3
lacI promoter
lac operator
RBS
pRSF-CBDG
AmpR promoter
T7 terminator
RBS
lac operator

GENETICALLY ENGINEERED BACTERIUM AND A PREPARATION METHOD AND USE THEREOF

CROSS-REFERENCE TO RELATED APPLICATION

This application is a U.S. National Phase Entry of International Application No. PCT/CN2022/124826 filed on Oct. 12, 2022, which claims priority to Chinese Patent Application No. 202111509981.9 filed on Dec. 10, 2021, which are hereby incorporated herein by reference in their entireties.

TECHNICAL FIELD

The invention relates to the field of microbial engineering, and in particular relates to a genetically engineered bacterium and a preparation method and use thereof.

BACKGROUND

Human milk oligosaccharide (HMO) is one of the components with high nutritional value in human milk. According to the monosaccharide composition and structural characteristics, HMOs can be categorized into neutral fucosyl, neutral non-fucosyl, sialic acid, etc. Among them, 2'-fucosyllactose (2'-fucosyllactose, 2'-FL) is the oligosaccharide with the highest content in human milk, and it is also one of the first HMOs approved by FDA and EU to be added to infant milk powder, dietary supplements and medical foods. 2'-FL has various functional activities such as regulating intestinal microbiome, preventing the adhesion of pathogenic bacteria, immunomodulating, and promoting the development and repair of the nervous system.

The main synthesis methods of 2'-FL include chemical synthesis, whole-cell synthesis and enzymatic synthesis, but there are many difficulties in the actual production process of chemical synthesis or enzymatic synthesis, such as stereochemical control, specific linkage formation, availability of raw materials, etc., synthesis with biosynthetic technology through microbial metabolism is more economical and efficient compared with chemical synthesis and enzymatic synthesis. GDP-fucose is synthesized from carbon sources such as glucose or glycerol using biosynthetic methods to simulate the metabolic mechanism of microorganisms themselves (or simulation), meanwhile fucosyl is transferred to lactose by exogenously expressed α-1,2-fucosyltransferase. This is the main method for industrial production of 2'-FL.

Since the lack of an appropriate post-translational processing mechanism in prokaryotic expression system, in the process of expressing exogenous proteins in *Escherichia coli* as the host bacteria, insoluble inclusion bodies will be formed due to incorrect protein folding, which again requires complex denaturation and renaturation, making it difficult to express large amounts of soluble exogenous proteins.

The fusion protein tag refers to the fusion of a protein sequence at the N-terminus or C-terminus of the protein, the purpose of which is to enhance the soluble expression of the recombinant protein, so as to improve the expression level of the recombinant protein in *E. coli*. Fusion protein tags provide an efficient strategy for the soluble expression of exogenous proteins in *E. coli*, but as there are many factors that result in the non-expression or very low levels of expression of exogenous protein in *E. coli*, such as the formation of inactive inclusion bodies due to incorrect folding during translation, or the formation of incorrectly paired disulfide bonds resulting in unstable protein expression, there may be different effects for different protein tags on promoting the expression of exogenous proteins in *E. coli*.

Patent CN112322565A of Jiangnan University discloses a method for improving the yield of 2'-fucosyllactose in recombinant *Escherichia coli*, which uses flexible linker to tag four different proteins: maltose binding protein (MBP), thioredoxin A (TrxA), ubiquitin-related small modification protein (SUMO), and transcription termination anti-termination factor (NusA), respectively fused to the N-terminus of α-1,2-fucosyltransferase FutC, and the constructed fusion protein FP-futC can increase the yield of 2'-FL from the catalyzed synthesis through to different levels. Among them, the yield of 2'-FL synthesized by TrxA-futC fusion protein was the highest, reaching 2.94 g/L, and the yield of 2'-FL synthesized by SUMO-futC fusion protein was 2.56 g/L. The TrxA-futC fusion protein gene was further integrated into the yjiP site on the genome of *Escherichia coli* MG1655 to obtain a plasmid-free 2'-FL genetically engineered strain MG-26ΔyjiP::trxA-futC, and the yield of 2'-FL after shake flask fermentation reached 3.85 g/L.

But the efficiency of producing 2'-fucosyllactose by the genetically engineered bacteria in the prior art is still not high enough, especially the yield is low during de novo synthesis.

SUMMARY

In view of the technical defects in the prior art, such as the low efficiency of the preparation method of 2'-fucosyllactose (2'-FL) and the poor function of the genetically engineered bacteria for producing 2'-fucosyllactose, the present invention provides a genetically engineered bacterium and a preparation method of 2'-fucosyllactose. The genetically engineered bacteria modulate the expression of some genes in the starting bacteria (such as *Escherichia coli*), especially by adding a protein tag to increase the expression of α-1,2-fucosyltransferase, so as to obtain a high-yield genetically engineered bacterium for 2'-fucosyllactose.

In order to solve the above-mentioned technical problems, a technical solution provided by the present invention is: a genetically engineered bacterium containing a gene encoding α-1,2-fucosyltransferase, and a gene encoding a protein tag is connected to the gene encoding α-1,2-fucosyltransferase (α-1,2-fucosyltranferase, abbreviated as futC in the present invention); the protein tag is MBP, SUMO1, SUMO2 or TrxA, the amino acid sequence of MBP is shown in SEQ ID NO: 2, the amino acid sequence of SUMO1 is shown in SEQ ID NO: 3, the amino acid sequence of SUMO2 is shown in SEQ ID NO: 4, the amino acid sequence of TrxA is shown in SEQ ID NO: 5.

In a preferred embodiment of the present invention, the amino acid sequence of the α-1,2-fucosyltransferase is shown in SEQ ID NO: 1.

In a specific embodiment of the present invention, the nucleotide sequence of the gene encoding the α-1,2-fucosyltransferase is shown in SEQ ID NO: 6.

In a preferred embodiment of the present invention, the nucleotide sequence of the gene encoding the MBP is shown in SEQ ID NO: 7, and the nucleotide sequence of the gene encoding the SUMO1 is shown in SEQ ID NO: 8, the nucleotide sequence of the gene encoding the SUMO2 is shown in SEQ ID NO: 9, and the nucleotide sequence of the gene encoding the TrxA is shown in SEQ ID NO: 10.

In a preferred embodiment of the present invention, the GDP-fucose degradation pathway of the genetically engineered bacteria is blocked. Preferably, all or part of the genes in the GDP-fucose degradation pathway in the genetically engineered bacteria are knocked out. More preferably, the wcaJ gene of the genetically engineered bacteria is knocked out.

In a preferred embodiment of the present invention, the GDP-mannose degradation pathway of the genetically engineered bacteria is blocked. Preferably, all or part of the genes in the GDP-mannose degradation pathway of the genetically engineered bacteria are knocked out. More preferably, the nudD and/or nudK genes of the genetically engineered bacteria are knocked out.

In a preferred embodiment of the present invention, the gene LacZ encoding the lactose operon beta-galactosidase of the genetically engineered bacteria is knocked out.

In a preferred embodiment of the present invention, the protein tag is located at the N-terminus of the α-1,2-fucosyltransferase.

In a specific embodiment of the present invention, the gene encoding the protein tag and the α-1,2-fucosyltransferase gene are linked together on a plasmid vector. Preferably, the plasmid is pET28a.

In a specific embodiment of the present invention, the starting bacteria of the genetically engineered bacteria is *Escherichia coli*, preferably BL21 strain.

In a preferred embodiment of the present invention, the genetically engineered bacteria overexpress one or more of the manC, manB, gmd and wcaG genes, and the amino acid sequences encoded by the manC, manB, gmd and wcaG genes are respectively shown in SEQ ID NOs: 95-98. Preferably, the nucleotide sequences of the manC, manB, gmd and wcaG genes are respectively shown in SEQ ID NOs: 91-94.

In the present invention, the manC gene is a mannose-1-phosphate guanylyltransferase gene. The manB gene is a phosphomannose mutase gene. The gmd gene is a GDP-D-mannose-4,6-dehydratase gene. The wcaG is a GDP-4-keto-6-deoxy-D-mannose-3,5-epimerase-4-reductase gene.

In order to solve the above-mentioned technical problems, a technical solution provided by the present invention is: a preparation method of 2'-fucosyllactose, which comprises: using lactose as a substrate, glycerol or glucose as a carbon source, fermenting the genetically engineered bacteria as described in the present invention, obtaining the 2'-fucosyllactose; preferably, the fermentation medium is TB medium.

In a preferred embodiment of the present invention, when the genetically engineered bacteria are fermented to an OD600 of 0.6-0.8, IPTG with a final concentration of 0.1-0.5 mM is added to the reaction system.

In a preferred embodiment of the present invention, the concentration of the glycerol or glucose is 5-50 g/L of glycerol, and the concentration of the lactose is 5-20 g/L.

In a specific embodiment of the present invention, when IPTG is added, the temperature of the fermentation is adjusted to 20-30° C., and the stirring is performed at a rotation speed of 150-300 rpm.

In a preferred embodiment of the present invention, a step of preparing the seed solution is further incorporated before the catalysis. Preferably, the step of preparing the seed solution comprises culturing the genetically engineered bacteria in LB medium. More preferably, the volume ratio of the seed liquid used in the fermentation to the liquid is 1:100.

In order to solve the above-mentioned technical problems, a technical solution provided by the present invention is: a recombinant expression vector, which comprises a gene encoding a protein tag and a gene encoding α-1,2-fucosyltransferase, and the protein tag is MBP, SUMO1, SUMO2 or TrxA, the amino acid sequence of the MBP is shown in SEQ ID NO: 2, the amino acid sequence of the SUMO1 is shown in SEQ ID NO: 3, and the amino acid sequence of SUMO2 is shown in SEQ ID NO: 4, the amino acid sequence of the TrxA is shown in SEQ ID NO: 5.

In a preferred embodiment of the present invention, the amino acid sequence of the α-1,2-fucosyltransferase is shown in SEQ ID NO: 1.

In a specific embodiment of the present invention, the nucleotide sequence of the gene encoding the MBP is shown in SEQ ID NO: 7, and the nucleotide sequence of the gene encoding the SUMO1 is shown in SEQ ID NO: 8, and the nucleotide sequence of the gene encoding the SUMO2 is shown in SEQ ID NO: 9, and the nucleotide sequence of the gene encoding the TrxA is shown in SEQ ID NO: 10.

In a specific embodiment of the present invention, the nucleotide sequence of the gene encoding the α-1,2-fucosyltransferase is shown in SEQ ID NO: 6;

In a specific embodiment of the present invention, the starting vector of the recombinant expression vector is pET28a plasmid vector.

In order to solve the above-mentioned technical problems, a technical solution provided by the present invention is: a method for preparing the genetically engineered bacteria of the present invention, comprising: transferring the recombinant expression vector of the present invention into *Escherichia coli* to obtain the genetically engineered bacteria.

In a preferred embodiment of the present invention, the method further comprises: knocking out the LacZ, wcaJ, nudD and/or nudK genes in the *E. coli.*

In a preferred embodiment of the present invention, the method further comprises: making the *E. coli* to overexpress manC, manB, gmd and/or wcaG genes, the amino acid sequences encoded by the manC, manB, gmd and wcaG genes are respectively shown in SEQ ID NOs: 95-98.

In a specific embodiment of the present invention, the *Escherichia coli* is a BL21 strain.

In a preferred embodiment of the present invention, the method further comprises: knocking out the LacZ, wcaJ, nudD and/or nudK genes in the *E. coli.*

In a preferred embodiment of the present invention, the method further comprises: making the *E. coli* to overexpress manC, manB, gmd and/or wcaG genes, the amino acid sequences encoded by the manC, manB, gmd and wcaG genes are respectively shown in SEQ ID NOs: 95-98.

In order to solve the above-mentioned technical problems, a technical solution provided by the present invention is: the use of the genetically engineered bacteria as described in the present invention or the recombinant expression vector as described in the present invention in the preparation of fucosyllactose, the fucosyllactose is preferably 2'-fucosyllactose.

On the basis of conforming to common knowledge in the art, the above preferred conditions can be combined arbitrarily to obtain preferred examples of the present invention.

The reagents and raw materials used in the present invention are all commercially available.

The positive progressive effect of the present invention lies in:

When the genetically engineered bacteria described in the present invention expresses the preferred α-1,2-fucosyltransferase of the present invention linked with a protein tag, it can greatly increase the 2'-fucosyllactose compared with the genetically engineered bacteria that only express α-1,2-fucosyltransferase exogenously, and the yield can be more than doubled in a preferred case.

DETAILED DESCRIPTION

In order to further illustrate the technical means adopted by the present invention and effects thereof, the following detailed description is given in conjunction with the accompanying drawings and the preferred examples of the present invention. The experimental methods in the following examples with no specific conditions are selected according to conventional methods and conditions, or according to the product insert.

BL21 (DE3) strain was purchased from Novagen Company, Cat. #69450-M; *Escherichia coli* Trans 10 competent cells were purchased from Beijing TransGen Biotech Co., Ltd.; plasmid extraction kit and gel recovery kit were purchased from Sangon Biotech (Shanghai) Co., Ltd., and SDS-PAGE kit was purchased from Shanghai Epizyme Biomedical Technology Co., Ltd.

In the examples, a high performance liquid chromatography (HPLC) system (SHIMADZU LC-20AD XR) was used to quantitatively detect the synthesis of 2'-FL in the fermentation broth of recombinant *Escherichia coli*, and the concentrations of 2'-FL and the substrate lactose in the fermentation broth were determined by HP-Amide column (Sepax, 4.6×250 mm 5 μm). The HPLC detector was a differential detector, the detection temperature of the chromatographic column was set to 35° C., the mobile phase was eluted by acetonitrile:water=68:32, and the detection flow rate was 1.4 ml/min.

Example 1 Construction of Chassis Strain FLIS009

Figure 2:
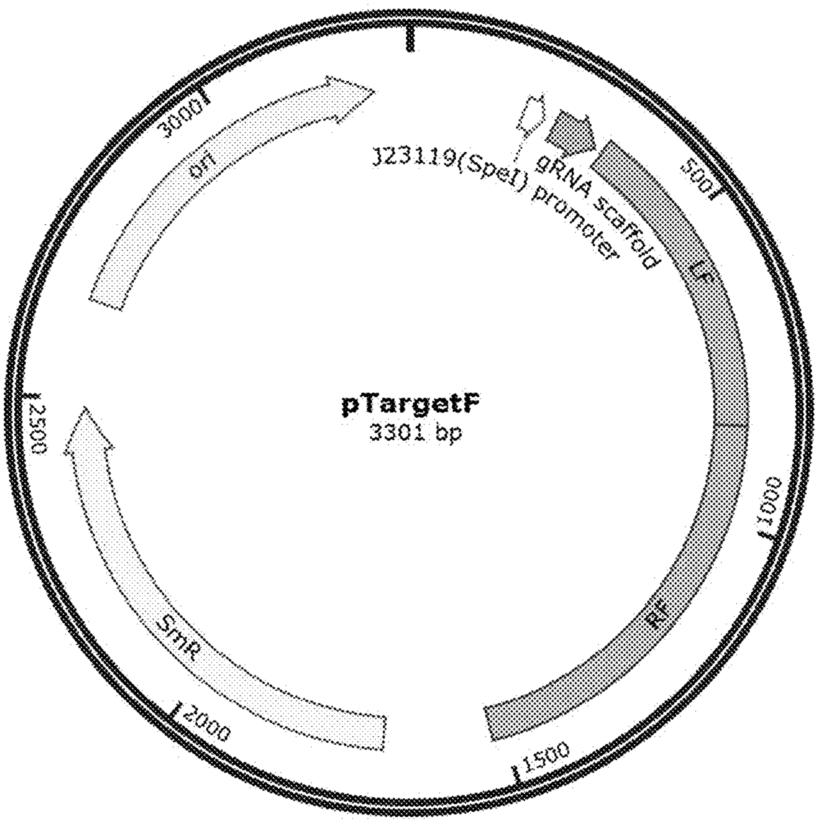
FIG. 2 is a profile of pTargetF plasmid.

1.1 Construction of Small Guide RNA (sgRNA) Plasmid for CRISPR/Cas9 Knockout System (1) The primers designed according to Table 3 (synthesized by Tsingke) were used for the specific amplification of each fragment using the pTargetF plasmid (see FIG. 2 for the profile) or the BL21 genome as a template, and the high-fidelity enzyme Primer Star Mix of Takala Company was used for PCR reaction, the reaction system is shown in the following Table 1:

TABLE 1

PCR amplification reaction system

| Agent | Volume added to the PCR reaction system |
|---|---|
| cDNA | 1 μl |
| Primer F | 1 μl |
| Primer R | 1 μl |
| PCR Mix | 12.5 μl |
| $ddH_2O$ | 9.5 μl |

The PCR amplification procedure is shown in the following Table 2:

TABLE 2

PCR reaction procedure

| Temperature | Time | Cycles |
|---|---|---|
| 98° C. | Pre-denaturation 3 min | |
| 98° C. | Denaturation 15 s | |
| 55° C. | Annealing 15 | 34 cycles |
| 72° C. | Extension 0.1 kb/s | |
| 72° C. | Extension 5 min | |
| 12° C. | Insulation | |

5 μl of the amplified product was subjected to 1% agarose electrophoresis to detect the amplification result. The target fragments were recovered by cutting gel using a gel recovery kit. The target fragments were ligated and recombined using NEB's multi-fragment recombinase, and the ligated recombination products were transformed into *E. coli* competent cells Trans 10. Sterilized LB liquid medium was added, cultured at 37° C. with shaking at 250 rpm for 1 h;

(2) The spot was picked onto the LB solid plate with spectinomycin added in advance, and inverted overnight at 37° C.;

(3) After the white single colony has grown, the white single colony was picked into a centrifuge tube containing 2 ml of LB liquid medium (containing 50 μg/ml spectinomycin), and cultured at 37° C. with shaking at 180 rpm for 6 hours;

(4) PCR detection was carried out on the bacterial liquid, 500 μl of the bacterial liquid verified as positive was sent to Tsingke Company for sequencing, and the remaining bacterial liquid was stored in 20% glycerol.

(5) The strains that were verified through sequencing were subjected to expanded culturing, and plasmid extraction was carried out by a plasmid extraction kit from Sangon. The sgRNA plasmids containing the BL21 genome were obtained and named as pTargetF-ΔLacZ, pTargetF-ΔnudK, pTargetF-ΔnudD, pTargetF-ΔwcaJ, respectively.

TABLE 3

Primer information for lacZ, nudK, nudD, wcaJ, etc gene knockout sgRNA plasmid construction

| Plasmid | Gene | Primer Name | Sequence | SEQ ID NO: | Template | Product Size (bp) |
|---|---|---|---|---|---|---|
| pTarget F- | pTarget F | GA001-P1-F4 | tgccgaccgtctagagtcgacctgca gaagcttag | 11 | pTargetF | 2000 bp |

TABLE 3-continued

Primer information for lacZ, nudK, nudD, wcaJ, etc gene knockout sgRNA plasmid construction

| Plasmid | Gene | Primer Name | Sequence | SEQ ID NO: | Template | Product Size (bp) |
|---|---|---|---|---|---|---|
| ΔLacZ | Backbone 1 | GA001-P1-R4 | aacTGGCGTTACCCAACTTAATCactagtattatacctaggactg | 12 | | |
| | PAM1 | GA001-P1-F1 | tagtGATTAAGTTGGGTAACGCCAgttttagagctagaaatagcaag | 13 | pTargetF | 150 bp |
| | | GA001-P1-R1 | gttccggaattcaaaaaaagcaccgactcggtgcc | 14 | | |
| | LF | GA001-LF | gctttttttgaattccggaacgggaaggcgactggagtg | 15 | BL21 Genome | 560 bp |
| | | GA001-P1-LR | ggtgcgggcctcgacggccagtgaatccgtaatcatg | 16 | | |
| | RF | GA001-P1-RR | tcgactctagacggtcggcaaagaccagaccgttc | 17 | BL21 Genome | 1800 bp |
| | | GA001-P1-RF | ctggccgtcgaggcccgcaccgatcgcccttc | 18 | | |
| pTarget F-ΔnudK | Donor-LF | nudK-f2 | tgaattcttcccttcctgaatcatctgcaaaaac | 19 | BL21 Genome | 500 bp |
| | | nudK-R2 | gtggagtcggtaaaataacaataatatttcgttg | 20 | | |
| | Donor-RF | nudK-F3 | attgttattttaccgactccacagcgcgaaatgaac | 21 | BL21 Genome | 500 bp |
| | | nudK-R3 | ctagaccggaagagccgtttatcaatacc | 22 | | |
| | pTarget F Backbone | nudK-F4 | gataaacggctcttccggtctagagtcgacctgcagaag | 23 | pTargetF | 2000 bp |
| | | nudK-R4 | ctaaaacGCGCAGCTTTCAATCAGCTGActagtattatacctaggactgag | 24 | | |
| | PAM | nudK-F1 | ctagtCAGCTGATTGAAAGCTGCGCgttttagagctagaaatagcaagttaa | 25 | pTargetF | 150 bp |
| | | nudK-R1 | gattcaggaagggaagaattcaaaaaaagcaccgactcggtgccac | 26 | | |
| pTarget F-ΔnudD | Donor-LF | pT-nudD-F2 | gctttttttgaattccacttcgtaatcctgaatatgcag | 27 | BL21 Genome | 500 bp |
| | | PT-nudD-R2 | cgctccactgattaccactggctgacgccggacgcac | 28 | | |
| | Donor-RF | PT-nudD-F3 | ccagtggtaatcagtggagcgcactaccgtggcaaagtcttcc | 29 | BL21 Genome | 500 bp |
| | | pT-nudD-R3 | cgactctagagacaacttccacccgagtaattcgcatgtg | 30 | | |
| | PAM1 | pT-nudD-F1 | ctagtgtgagtggtgaaatccgtgcgttttagagctagaaatagcaag | 31 | pTargetF | 150 bp |
| | | pT nudD-R1 | gattacgaagtggaattcaaaaaaagcaccgactcgg | 32 | | |
| | pTarget F Backbone | pT-nudD-F4 | ggtggaagttgtctctagagtcgacctgcagaagcttag | 33 | pTargetF | 2000 bp |
| | | PT-nudD-R4 | ctaaaacgcacggatttcaccactcacactagtattatacctaggactgagc | 34 | | |
| pTarget F-ΔwcaJ | Donor-LF | wcaJ-F2 | cgagtcggtgctttttttgaattcgacagcggcatgatcccgtggctg | 35 | BL21 Genome | 550 bp |
| | | wcaJ-R2 | cgccacgccagcccaacaggtgcatgtagaggaatg | 36 | | |
| | Donor-RF | wcaJ-F3 | catgcacctgttgggctggcgtggcgaaaccgacacg | 37 | BL21 Genome | 550 bp |
| | | wcaJ-R3 | cagggtaatagatctaagcttgcgcggaactgctgtccgtgggg | 38 | | |
| | PAM1 | wcaJ-F1 | gtcctaggtataatactagtcatcgccgcagcggtttcaggttttagaget | 39 | pTargetF | 150 bp |
| | | wcaJ-R1 | cagccacgggatcatgccgctgtcgaattcaaaaaaagcaccgactcg | 40 | | |

TABLE 3-continued

Primer information for lacZ, nudK, nudD, wcaJ, etc gene knockout sgRNA plasmid construction

| Plasmid | Gene | Primer Name | Sequence | SEQ ID NO: | Template | Product Size (bp) |
|---|---|---|---|---|---|---|
| | pTarget F | wcaJ-F4 | ccccacggacagcagttccgcgcaa gcttagatctattaccctg | 41 | pTargetF | 2000 bp |
| | Backbone | wcaJ-R4 | gctctaaaacctgaaaccgctgcggc gatgactagtattatacct | 42 | | |

(1) Preparation of BL21 competent cells: single colony streak culture was performed on the strain BL21 stored at −80° C.; a single colony was picked and inoculated to 5 ml of LB medium, and cultured at 37° C. with shaking at 200 rpm until the OD was about 0.5 (about 3 h), then the culture was ice-bathed for 30 min; the bacterial liquid was transferred to a pre-cooled sterile centrifuge tube, centrifuged at 4000 rpm for 10 min at 4° C., the supernatant was discarded, and the bacteria was collected; the cells were resuspended with pre-cooled sterile water, centrifuged at 4000 rpm for 10 min at 4° C., the supernatant was discarded; the cells were resuspended twice with a solution containing 0.1 M $CaCl_2$), centrifuged at 4000 rpm for 10 min at 4° C., and the supernatant was discarded; finally, the cells were resuspended with an appropriate amount of 0.1 M $CaCl_2$) solution containing 15% glycerol, dispensed into 1.5 ml centrifuge tubes with 100 ul per tube, quickly frozen in liquid nitrogen, and stored at −80° C.

(2) 3 ul pCas-sac plasmid was added to 100 μL *E. coli* BL21 competent, placed on ice for 30 min, then heat-shocked at 42° C. for 45 s, and immediately placed on ice for 2-5 min; after adding 800 μL of LB, it was placed on a shaker at 30° C. and incubated for 45 min, followed by plating (Km resistant, LB medium), and was placed upside down in a 30° C. incubator, and cultured overnight; spots were picked to LB medium (Kana resistant), cultured for several hours before bacteria preservation (final concentration of glycerol 30%).

Figure 1:
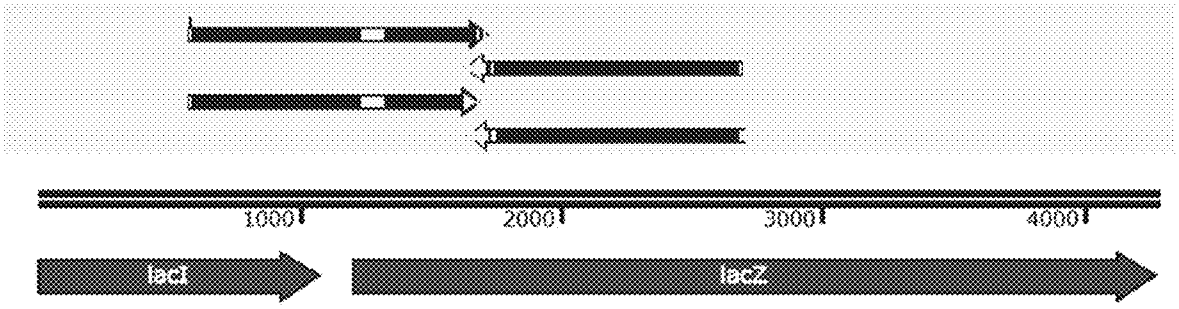
FIG. 1 is a profile of the lacZ knockout verification.

(3) The pCas-sac/BL21 transformants were picked and inoculated into LB sieve tubes (Kana resistant) and cultured at 30° C. until OD=0.2, then arabinose with a final concentration of 2 g/L was added for induction, and at OD=0.4, the competent preparation was carried out, the preparation method is the same as operation (1);

(4) The correctly constructed pTargetF-ΔLacZ plasmids were transformed into pCas-sac/BL21 competent cells by heat shock method, coated on LB plates (k+, spe+) after recovery, and cultured at 30° C. overnight;

(5) PCR verification was carried out on a single colony on the resistant plate, with verification primers shown in Table 4, and the sequencing verification profile shown in FIG. 1, and the LacZ gene knockout strain was verified;

(6) The strains with LacZ gene knockout were picked and shaken, and rhamnose with a final concentration of 10 mM was added to induce the loss of the sgRNA plasmid pTargetF-ΔLacZ;

(7) Streaking to verify whether the pTargetF-ΔLacZ plasmid was lost (see Table 4 for primers), and the LacZ gene knockout strains with sgRNA loss were named as FLIS001.

1.2.2 Knockout of GDP-Fucose Degradation Related Gene wcaJ Based on FLIS001 Strain FLIS001 competent preparation and knockout were the same as in 1.2.1. The pTargetF-ΔwcaJ plasmid was used to knock out the wcaJ gene. The method was the same as that in 1.2.1, the wcaJ gene knockout strain was obtained and named as FLIS007.

1.2.3 Knockout of GDP-Mannose Degradation Related Genes nudD and nudK Based on FLIS007 Strain (1) The nudD gene in the FLIS007 strain was knocked out using the pTargetF-ΔnudD plasmid, and the method is the same as that in (1), the knockout strain was named as FLIS008.

(2) The nudK gene was knocked out on the basis of the FLIS008 strain using the pTargetF-ΔnudK plasmid, and the method is the same as that in 1.2.1, the knockout strain was named as as FLIS009.

(3) Loss of sgRNA plasmid was performed in FLIS009 strain, the method is the same as that in 1.2.1.

(4) Loss of pCas-SAC plasmid was performed in FLIS009 strain: the FLIS009 strain with sgRNA loss was inoculated on an antibiotic free LB plate containing 10 g/L sucrose, cultured at 37° C., and PCR validation was performed with pCas-SAC verification primers in Table 4 to ensure that the pCas-SAC plasmid free chassis strain FLIS009 was obtained.

TABLE 4

Gene knockout validation primers for LacZ, wcaJ, nudD, nudK and the like

| Strain | Knockout Gene | Primer Name | Primer Sequence | SEQ ID NO: | Product Size (bp) |
|---|---|---|---|---|---|
| FLIS001 | LacZ | LacZ-YZ1-F | cgcgctgttagcgggcccattaagttctg | 43 | 2000 bp after knockout |
| | | LacZ-YZ2-R | ggtcttcatccacgcgcgcgtacatcgg | 44 | |

TABLE 4-continued

Gene knockout validation primers for LacZ, wcaJ, nudD, nudK and the like

| Strain | Knockout Gene | Primer Name | Primer Sequence | SEQ ID NO: | Product Size (bp) |
|---|---|---|---|---|---|
| FLIS007 | wcaJ | wcaJ-YZ-for | gtcggcctgttggcagaagcattc | 45 | 1.5 kb after knockout |
| | | wcaJ-YZ-R | gtagccaaacagcagcgttcttaccgcac | 46 | |
| FLIS008 | nudD | nudD-YZ-F | ccgtcgccagctgtgccactttg | 47 | 1.2 kb after knockout |
| | | nudD-YZ-R | caaactgtgcgaatcttacaatcgcc | 48 | |
| FLIS009 | nudK | nudK-YZ-F | gctgagcatcaataaacaacaacgctg | 49 | 1.4 kb after knockout |
| | | nudK-YZ-R | atgaagatgcgccgggcgtttatg | 50 | |
| sgRNA Plasmid | | CX-targetF-F | cagcgagtcagtgagcgag | 51 | 2000 bp |
| | | CX-targetF-R | gacattgcactccaccgct | 52 | |
| pCas-SAC | | Kan-F | gaaggagaaaactcaccgag | 53 | 3300 bp |
| | | Pcr4-R1 | cagctgcataaaattgcgattggcaaaaccatc | 54 | |

Example 2 Production of 2'-FL Using FLIS009 Strain 2.1 Construction of Expression Plasmid for 2'-FL Synthesis 2.1.1 Construction of Plasmid pRSF-CBDG manC gene is a mannose-1-phosphate guanylyltransferase gene; manB gene is a phosphomannose mutase gene; gmd gene is a GDP-D-mannose-4,6-dehydratase gene; wcaG is a GDP-4-keto-6-deoxy-D-mannose-3,5-epimerase-4-reductase gene.

The primers designed according to Table 5 (synthesized by Tsingke) were used for the specific amplification of each fragment using the pRSFDuet plasmid or the BL21 genome as the template. See 1.1 for the amplification method.

(2) The recovery, ligation and recombination, competent transformation and ampicillin resistance screening of amplified products were carried out according to the method in 1.1;

(3) Positive colonies were selected for PCR verification, 500 μl of the bacterial liquid verified as positive was sent to Tsingke Company for sequencing, and the remaining bacterial solution was stored in 20% glycerol.

Figure 3:
FIG. 3 is a profile of RSF-CBDG plasmid.

(4) The strains that were verified through sequencing were subjected to expanded culturing, and plasmid extraction was carried out by a plasmid extraction kit from Sangon to obtain a plasmid containing manC, manB, gmd, and wcaG genes, which is named as pRSF-CBDG plasmid (see FIG. 3).

TABLE 5

Primer information for plasmid RSF-CBDG construction

| Plasmid | Gene | Primer Name | Primer Sequence | SEQ ID NO: | Template | Product Size (bp) |
|---|---|---|---|---|---|---|
| pRSF-CBDG | manC | CBGW-manC-F | taaggagatataccatggcgcagtcgaaactcta | 55 | BL21 Genome | 1437 bp |
| | | CBGW-manC-R | gttaatttttcatggtatatctccttttacacccgtccgtagcg | 56 | | |
| | manB | CBGW-manB-F | cggacgggtgtaaaaggagatataccatgaaaaaattaacctgctttaaag | 57 | BL21 Genome | 1371 bp |
| | | CBGW-manB-R | gagctcgaattcttactcgttcagcaacgtcag | 58 | | |
| | gmd | CBGW-gmd-F | gaaggagatatacaatgtcaaaagtcgctctcat | 59 | BL21 Genome | 1122 bp |
| | | CBGW-gmd-R | gttgtttactcatggtatatctccttttatgactccagcgcgatcg | 60 | | |
| | wcaG | CBGW-wcaG-F | ctggagtcataaaaggagatataccatgagtaaacaacgagtttttattg | 61 | BL21 Genome | 966 bp |
| | | CBGW-wcaG-R | tggcagcagcctaggttacccccgaaagcggtct | 62 | | |
| | pRSF Duet | CBGW-F1 | gctttcgggggtaacctaggctgctgccaccg | 63 | pRSFDuet | 3395 bp |
| | Backbone 1 | CBGW-R1 | cgactgcgccatggtatatctccttattaaagttaaac | 64 | | |

TABLE 5-continued

Primer information for plasmid RSF-CBDG construction

| Plasmid | Gene | Primer Name | Primer Sequence | SEQ ID NO: | Template | Product Size (bp) |
|---|---|---|---|---|---|---|
| | pRSF Duet Backbone 2 | CBGW-F2 | ttgctgaacgagtaagaattcgagctcggcgcg | 65 | pRSFDuet | 187 bp |
| | | CBGW-R2 | gcgacttttgacattgtatatctccttcttatacttaac | 66 | | |

The amino acid sequences of manC, manB, gmd and wcaG are respectively shown in SEQ ID NOs: 95-98, and the nucleotide sequences are respectively shown in SEQ ID NOs: 91-94.

2.1.2 Construction of α-1,2-Fucosyltransferase futC Expression Plasmid

α-1,2-fucosyltransferase futC (GT007), MBP, SUMO1, SUMO2, TrxA sequences (amino acid sequences are respectively shown in SEQ ID NOs: 1-5, nucleotide sequences are respectively shown in SEQ ID NOs: 6-10) were synthesized by Sangon Company. The primers designed according to Table 6 (synthesized by Tsingke) were used for the specific amplification of each fragment using the pET28a plasmid or the BL21 genome as the template. See 1.1 for the amplification method.

(1) The recovery of amplified products, ligation and recombination, competent transformation and Kana resistance screening were carried out according to the method in 1.1;

(2) Positive colonies were selected for PCR verification, 500 μl of the bacterial liquid that was verified to be positive was sent to Tsingke Company for sequencing, and the remaining bacterial solution was stored in 20% glycerol.

(3) The strains that were verified through sequencing were subjected to expanded culturing, and plasmid extraction was carried out by a plasmid extraction kit from Sangon to obtain futC expression plasmids with different tags, which are named as pET-MBP-futC, pET-SUMO1-futC, pET-SUMO2-futC, pET-TrxA-futC plasmid, pET-futC, respectively.

TABLE 6

Primer information for futC expression plasmid construction

| Plasmid | Gene | Primer Name | Primer Sequence | SEQ ID NO: | Template | Product Size (bp) |
|---|---|---|---|---|---|---|
| pET-MBP-futC | MBP | FL121-MBP-F | AAGGAGATATACCATGaaaatcgaagaaggtaa | 67 | MBP | 1203 bp |
| | | FL121-MBP-R | GATGCTCATatGGAATTcggatccctgaaaat | 68 | | |
| | futC | FL121-futC-F | cagggatccgAATTCCatATGAGCATCATCCGTCT | 69 | GT007 | 897 bp |
| | | FL121-futC-R | GTGCGGCCGCAAGCttaGCAGCTGCTGTGTTTATCAAC | 70 | | |
| | pET Back-bone | FL121-F | ACAGCAGCTGCtaaGCTTGCGGCCGCACTCGAGCAC | 71 | pET28a | 5246 bp |
| | | FL121-R | tcttcgattttCATGGTATATCTCCTTCTTAAAGTTA | 72 | | |
| pET-SUMO1-futC | SUMO1 | FL122-SUMO1-F | AAGGAGATATACCatgtcggactcagaagtcaa | 73 | SUMO1 | 294 bp |
| | | FL122-SUMO1-R | GATGCTCATatGaccaccaatctgttctctgt | 74 | | |
| | futC | FL122-futC-F | acagattggtggtCatATGAGCATCATCCGTCT | 75 | GT007 | 897 bp |
| | | FL122-futC-R | GTGCGGCCGCAAGCttaGCAGCTGCTGTGTTTATCAAC | 76 | | |
| | pET Back-bone | FL122-F | ACAGCAGCTGCtaaGCTTGCGGCCGCACTCGAGCAC | 71 | pET28a | 5246 bp |
| | | FL122-R | ctgagtccgacatGGTATATCTCCTTCTTAAAGT | 77 | | |
| pET-SUMO2-futC | SUMO2 | FL123-SUMO2-F | gGAAGGAGATATACCATGGGCCATCATCATCACCA | 78 | SUMO2 | 306 bp |
| | | FL123-SUMO2-R | TGATGCTCATatGACCACCGGTCTGTTGCTGA | 79 | | |
| | futC | FL123-futC-F | ACAGACCGGTGGTCatATGAGCATCATCCGTCTG | 80 | GT007 | 897 bp |
| | | FL123-futC-R | GTGCGGCCGCAAGCttaGCAGCTGCTGTGTTTATCAAC | 81 | | |
| | pET Back-bone | FL123-F | ACAGCAGCTGCtaaGCTTGCGGCCGCACTCGAGCAC | 71 | pET28a | 5246 bp |
| | | FL123-R | ATGATGATGGCCCATGGTATATCTCCTTCTTAAAGTTA | 82 | | |

TABLE 6-continued

Primer information for futC expression plasmid construction

| Plasmid | Gene | Primer Name | Primer Sequence | SEQ ID NO: | Template | Product Size (bp) |
|---|---|---|---|---|---|---|
| pET-TrxA-futC | TrxA | FL124-TrxA-F | AGGAGATATACCatgagcgataaa attattca | 83 | TrxA | 567 bp |
| | | FL124-TrxA-R | TGATGCTCATatGgaatteggatccc tgaaaat | 84 | | |
| | futC | FL124-futC-F | agggatccgaattcCatATGAGCATC ATCCGTCT | 85 | GT007 | 897 bp |
| | | FL124-futC-R | GTGCGGCCGCAAGCttaGCAG CTGCTGTGTTTATCAAC | 86 | | |
| | pET Back-bone | FL124-F | ACAGCAGCTGCtaaGCTTGCG GCCGCACTCGAGCAC | 71 | pET28a | 5246 bp |
| | | FL124-R | ttttatcgctcatGGTATATCTCCTT CTTAAAG | 87 | | |
| pET-futC | futC | FAB-futC-F | CGCGCGGCAGCCATCatATG AGCATCATCCGTCTGCA | 88 | GT007 | 897 bp |
| | | 28A-GT008-R | GTGCGGCCGCAAGCttaGCAG CTGCTGTGTTTATCAAC | 89 | | |
| | pET Back-bone | 28A-GT008-F2 | ACAGCAGCTGCtaaGCTTGCG GCCGCACTCGAGCAC | 71 | pET28a | 5246 bp |
| | | FAB-R1 | GATGATGCTCATatGATGGCT GCCGCGCGGCAC | 90 | | |

2.2 Production of 2'-FL During Fermentation 2.2.1 Construction of 2'-FL Producing *E. coli* Strains Competent cells were prepared based on the gene knockout strain FLIS009, the specific method was the same as that in 1.2.1, and then the plasmids pRSF-CBDG+pET-MBP-futC, pRSF-CBDG+pET-SUMO1-futC, pRSF-CBDG+pET-SUMO2-futC, pRSF-CBDG+pET-TrxA-futC, pRSF-CBDG+pET-futC were respectively transferred into FLIS009 competent cells, and screened for correct clones on LB plate (100 μg/ml ampicillin, 50 μg/ml kana antibiotics). The strain *E. coli* FLIS009-FL carrying the 2'-FL synthesis pathway was verified by PCR and named as FLIS201, FLIS202, FLIS203, FLIS204, FLIS205, respectively.

2.2.2 Producing 2'-FL with FLIS009-FL Strain (1) TB medium: trypton 12 g (Trypton Oxoid LP0042 73049-73-7 BR), yeast extract 24 g, glycerol 4 ml, 2.31 g $KH_2PO_4$ and 12.54 g $K_2HPO_4$ were diluted to 1000 ml with deionized water, sterilized at 121° C. for 30 min, and stored at room temperature.

(2) LB medium: 10 g of tryptone was weighed respectively, distilled water was added at a ratio of 1:4 (mass to volume ratio, g/mL) to dissolve and mix, the pH was adjusted to 7.2 with 1 mol/L NaOH, and the liquid was diluted to 1 L, sterilized at 121° C. for 30 min, and stored at 4° C. without adding agar to the LB liquid.

(3) 1000 g/L glycerol: 1000 g glycerol was weighed, diluted to 1 L with deionized water, sterilized at 121° C. for 30 min, and stored at room temperature.

(4) 250 g/L lactose: 250 g lactose was dissolved in deionized water (dissolve by heating), diluted to 1 L, sterilized at 121° C. for 30 minutes, and stored at room temperature.

(5) Preparation of seed solution: the strains were inoculated into 5 mL of LB medium (containing 100 μg/ml ampicillin and 50 μg/ml kana antibiotics), and cultured at 37° C., 250 rpm for 4 hours.

(6) Fermentation culture: the seed liquid was inoculated into fresh fermentation medium (TB medium) with a ratio of seed liquid:medium=1:100 (v/v), cultivated at 37° C., 220 rpm until OD600 is 0.8, then IPTG (to a final concentration of 0.2 mM), 2 ml of 1000 g/L glycerol (to a final concentration of 20 g/L) and 4 ml of 250 g/L lactose (to a final concentration of 10 g/L) were added, the resultant was cultured at 25° C., 220 rpm to induce protein expression and fermentation culture.

(7) Sample processing method: 2-3 ml of fermentation broth was taken to lyse the cells by repeatedly freezing and thawing, the resultant was put in boiling water for 20 minutes after lysis, and then centrifuged (4° C., 12000 rpm for 5 minutes), the pellet was removed and the supernatant was kept and passed through a 0.22 μm filter membrane, and the content of 2'-FL in each treatment was detected by differential detection method.

2.3 Shake Flask Fermentation Validation

The strain obtained in 2.2.2 (1) was inoculated into TB medium according to 2.2.2(5), and cultured under the conditions of 25° C. and 220 rpm to induce protein expression and fermentation.

(2) The fermentation broth was taken for sample processing and 2'-FL content detection according to the method in 2.2.2 (6). The results are shown in Table 7.

TABLE 7

2'-FL yield

| Strain | Plasmid | 2'-FL Yield (g/L) |
|---|---|---|
| FLIS201 | RSF-CBDG + pET-MBP-futC | 4.79 |
| FLIS202 | RSF-CBDG + pET-SUMO1-futC | 4.92 |
| FLIS203 | RSF-CBDG + pET-SUMO2-futC | 4.28 |
| FLIS204 | RSF-CBDG + pET-TrxA-futC | 4.09 |
| FLIS205 | RSF-CBDG + pET-futC | 2.25 |

Figure 4:
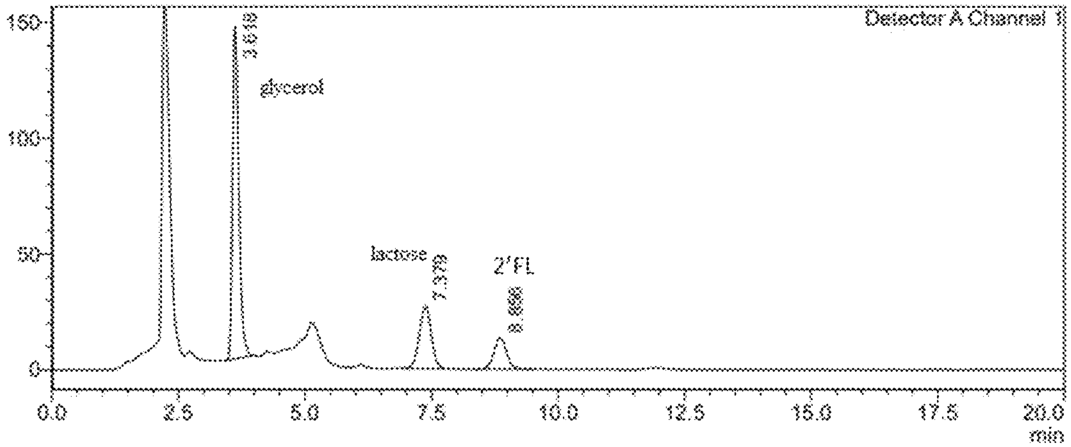
FIG. 4 is a graph showing the detection of 2'-FL content in FLIS202 fermentation broth.

(3) From Table 7, it can be seen that the 2'-FL yield of tagged FLIS202 is significantly higher than that of untagged FLIS205, as shown in FIG. 4.

The invention claimed is:

1. A genetically engineered bacterium, characterized in containing a gene encoding α-1,2-fucosyltransferase fused to a protein tag, wherein an amino acid sequence of the α-1,2-fucosyl transferase comprises SEQ ID NO: 1; the protein tag is maltose binding protein (MBP) or thioredoxin A (TrxA), an amino acid sequence of the MBP comprises SEQ ID NO: 2, and an amino acid sequence of the TrxA comprises SEQ ID NO: 5.

2. The genetically engineered bacterium as claimed in claim 1, wherein a nucleotide sequence of the gene encoding the α-1,2-fucosyltransferase is shown in SEQ ID NO: 6;
- and/or, a nucleotide sequence of the gene encoding the MBP is shown in SEQ ID NO: 7, and a nucleotide sequence of the gene encoding the TrxA is shown in SEQ ID NO: 10.

3. A preparation method of 2'-fucosyllactose, comprising: taking lactose as a substrate, glycerol or glucose as a carbon source, fermenting the genetically engineered bacterium as claimed in claim 2 to obtain the 2'-fucosyllactose.

4. The genetically engineered bacterium as claimed in claim 1, wherein a GDP-fucose degradation pathway of the genetically engineered bacterium is blocked;
- and/or, a GDP-mannose degradation pathway of the genetically engineered bacterium is blocked;
- and/or, LacZ gene encoding a lactose operon β-galactosidase of the genetically engineered bacterium is knocked out;
- and/or, the starting bacterium of the genetically engineered bacterium is *Escherichia coli;*
- and/or, the genetically engineered bacterium overexpresses one or more of manC, manB, gmd and wcaG genes, and amino acid sequences encoded by the manC, manB, gmd and wcaG genes are respectively shown in SEQ ID NOs: 95-98.

5. The genetically engineered bacterium as claimed in claim 4, wherein all or part of the genes in the GDP-fucose degradation pathway of the genetically engineered bacterium are knocked out; and/or, all or part of the genes in the GDP-mannose degradation pathway of the genetically engineered bacterium are knocked out.

6. The genetically engineered bacterium as claimed in claim 5, wherein wcaJ gene of the genetically engineered bacterium is knocked out; and/or, nudD and/or nudK genes of the genetically engineered bacterium are knocked out.

7. A preparation method of 2'-fucosyllactose, comprising: taking lactose as a substrate, glycerol or glucose as a carbon source, fermenting the genetically engineered bacterium as claimed in claim 4 to obtain the 2'-fucosyllactose.

8. A preparation method of 2'-fucosyllactose, comprising: taking lactose as a substrate, glycerol or glucose as a carbon source, fermenting the genetically engineered bacterium as claimed in claim 1 to obtain the 2'-fucosyllactose.

9. The preparation method as claimed in claim 8, further comprising adding IPTG to a final concentration of 0.1-0.5 mM when the genetically engineered bacterium is fermented until OD600 is 0.6-0.8.

10. The preparation method as claimed in claim 9, wherein a concentration of the glycerol or glucose is 5-50 g/L, and a concentration of lactose is 5-20 g/L; and/or, when the IPTG is added, the temperature during the fermenting is adjusted to 20-30° C., and stirring is performed at a rotational speed of 150-300 rpm.

11. A method of preparation of fucosyllactose comprising using the genetically engineered bacterium as claimed in claim 1.

12. The method as claimed in claim 11, wherein the fucosyllactose is 2'-fucosyllactose.

13. A recombinant expression vector comprising a gene encoding α-1,2-fucosyltransferase fused to a protein tag, the protein tag is maltose binding protein (MBP) or thioredoxin A (TrxA), an amino acid sequence of the MBP comprises SEQ ID NO: 2, and an amino acid sequence of the TrxA comprises SEQ ID NO: 5, and an amino acid sequence of the α-1,2-fucosyltransferase comprises SEQ ID NO: 1.

14. The recombinant expression vector as claimed in claim 13, wherein a nucleotide sequence of the gene encoding the α-1,2-fucosyltransferase is shown in SEQ ID NO: 6; and/or a nucleotide sequence of the gene encoding the MBP is shown in SEQ ID NO: 7, and a nucleotide sequence of the gene encoding the TrxA is shown in SEQ ID NO: 10.

15. A method for preparing a genetically engineered bacterium, comprising: transferring the recombinant expression vector as claimed in claim 14 into *Escherichia coli* to obtain the genetically engineered bacterium.

16. The method as claimed in claim 15, further comprising: knocking out LacZ, wcaJ, nudD and/or nudK genes in the *Escherichia coli*; and/or overexpressing manC, manB, gmd and/or wcaG gene in the *Escherichia coli*, wherein amino acid sequences encoded by manC, manB, gmd and wcaG genes are respectively shown in SEQ ID NOs: 95-98.

17. A method for preparing a genetically engineered bacterium, comprising: transferring the recombinant expression vector as claimed in claim 13 into *Escherichia coli* to obtain the genetically engineered bacterium.

18. The method as claimed in claim 17, further comprising: knocking out LacZ, wcaJ, nudD and/or nudK genes in the *Escherichia coli*; and/or overexpressing manC, manB, gmd and/or wcaG gene in the *Escherichia coli*, wherein amino acid sequences encoded by manC, manB, gmd and wcaG genes are respectively shown in SEQ ID NOs: 95-98.

* * * * *

SEQUENCE LISTING

```
Sequence total quantity: 98
SEQ ID NO: 1            moltype = AA  length = 300
FEATURE                 Location/Qualifiers
REGION                  1..300
                        note = alpha-1,2-fucosyltransferase futC (GT007) amino acid
                         sequence
source                  1..300
                        mol_type = protein
                        organism = synthetic construct
SEQUENCE: 1
MAFKVVQICG GLGNQMFQYA FAKSLQKHLN TPVLLDTTSF DWSNRKMQLE LFPIDLPYAN  60
AKEIAIAKMQ HLPKLVRDAL KYIGFDRVSQ EIVFEYEPKL LKPSRLTYFF GYFQDPRYFD  120
AISSLIKQTF TLPPPPENNK NNNKKEEEYQ RKLSLILAAK NSVFVHIRRG DYVGIGCQLG  180
IDYQKKALEY MAKRVPNMEL FVFCEDLKFT QNLDLGYPFT DMTTRDKEEE AYWDMLLMQS  240
CKHGIIANST YSWWAAYLME NPEKIIIGPK HWLFGHENIL CKEWVKIESH FEVKSQKYNA  300

SEQ ID NO: 2            moltype = AA  length = 401
FEATURE                 Location/Qualifiers
REGION                  1..401
                        note = MBP
source                  1..401
                        mol_type = protein
                        organism = synthetic construct
SEQUENCE: 2
MKIEEGKLVI WINGDKGYNG LAEVGKKFEK DTGIKVTVEH PDKLEEKFPQ VAATGDGPDI  60
IFWAHDRFGG YAQSGLLAEI TPDKAFQDKL YPFTWDAVRY NGKLIAYPIA VEALSLIYNK  120
DLLPNPPKTW EEIPALDKEL KAKGKSALMF NLQEPYFTWP LIAADGGYAF KYENGKYDIK  180
DVGVDNAGAK AGLTFLVDLI KNKHMNADTD YSIAEAAFNK GETAMTINGP WAWSNIDTSK  240
VNYGVTVLPT FKGQPSKPFV GVLSAGINAA SPNKELAKEF LENYLLTDEG LEAVNKDKPL  300
GAVALKSYEE ELAKDPRIAA TMENAQKGEI MPNIPQMSAF WYAVRTAVIN AASGRQTVDE  360
ALKDAQTNSG TGGGSGDDDD KSPMGEDIPT TENLYFQGSE F                     401

SEQ ID NO: 3            moltype = AA  length = 98
FEATURE                 Location/Qualifiers
REGION                  1..98
                        note = SUMO1
source                  1..98
                        mol_type = protein
                        organism = synthetic construct
SEQUENCE: 3
MSDSEVNQEA KPEVKPEVKP ETHINLKVSD GSSEIFFKIK KTTPLRRLME AFAKRQGKEM  60
DSLRFLYDGI RIQADQTPED LDMEDNDIIE AHREQIGG                         98

SEQ ID NO: 4            moltype = AA  length = 102
FEATURE                 Location/Qualifiers
REGION                  1..102
                        note = SUMO2
source                  1..102
                        mol_type = protein
                        organism = synthetic construct
SEQUENCE: 4
MGHHHHHHGS LQEEKPKEGV KTENDHINLK VAGQDGSVVQ FKIKRHTPLS KLMKAYCERQ  60
GLSMRQIRFR FDGQPINETD TPAQLEMEDE DTIDVFQQQT GG                     102

SEQ ID NO: 5            moltype = AA  length = 189
FEATURE                 Location/Qualifiers
REGION                  1..189
                        note = TrxA
source                  1..189
                        mol_type = protein
                        organism = synthetic construct
SEQUENCE: 5
MSDKIIHLTD DSFDTDVLKA DGAILVDFWA EWCGPCKMIA PILDEIADEY QGKLTVAKLN  60
IDQNPGTAPK YGIRGIPTLL LFKNGEVAAT KVGALSKGQL KEFLDANLAG SGSGHMHHHH  120
HHSSGLVPRG SGMKETAAAK FERQHMDSPD LGTDDDDKAM GSHHHHHHHH GSDYDIPTTE  180
NLYFQGSEF                                                         189

SEQ ID NO: 6            moltype = DNA  length = 907
FEATURE                 Location/Qualifiers
misc_feature            1..907
                        note = alpha-1,2-fucosyltransferase futC (GT007) nucleotide
                         sequence
source                  1..907
                        mol_type = other DNA
                        organism = synthetic construct
SEQUENCE: 6
atggcgttca aagttgttca gatctgcggc ggtctgggta accagatgtt ccagtacgcg  60
ttcgcgaaaa gcctgcagaa acacctgaac accccggttc tgctggatac caccagcttc  120
```

```
gattggagca accgtaaaat gcagctggaa ctgttcccga tcgatctgcc gtacgcgaac  180
gcgaaagaaa tcgcgatcgc gaaaatgcag cacctgccga aactggttcg tgatgcgctg  240
aaatacatcg gcttcgatcg tgttagccag gaaatcgttt tcgaatacga accgaaactg  300
ctgaaaccga gccgtctgac ctacttcttc ggttacttcc aggacccgcg ttacttcgat  360
gcgatctcta gcctgatcaa acagaccttc accctgccgc cgccgccgga aaacaacaaa  420
aacaacaaca aaaaagaaga agaataccag cgtaaactga gcctgatcct ggcggcgaaa  480
aacagcgttt tcgttcacat ccgtcgtggt gactacgttg gtatcggctg ccagctgggt  540
atcgattacc agaaaaaagc gctggaatac atggcgaaac gtgttccgaa catggaactg  600
ttcgttttct gcgaagatct gaaattcacc cagaacctgg atctgggcta cccgttcacc  660
gatatgacca cccgtgataa agaagaagaa gcgtactggg atatgctgct gatgcagtct  720
tgcaaacacg gcatcatcgc gaacagcacc tactcttggt gggcggcgta cctgatggaa  780
aacccggaaa aaatcatcat cggtccgaaa cactggctgt tcggtcacga aaacatcctg  840
tgcaaagaat gggttaaaat cgaatcccac ttcgaagtta aatctcagaa atacaacgcg  900
taagctt                                                             907

SEQ ID NO: 7           moltype = DNA  length = 1203
FEATURE                Location/Qualifiers
misc_feature           1..1203
                       note = MBP
source                 1..1203
                       mol_type = other DNA
                       organism = synthetic construct
SEQUENCE: 7
atgaaaatcg aagaaggtaa actggtaatc tggattaacg gcgataaagg ctataacggt  60
ctcgctgaag tcggtaagaa attcgagaaa gataccggaa ttaaagtcac cgttgagcat  120
ccggataaac tggaagagaa attcccacag gttgcggcaa ctggcgatgg ccctgacatt  180
atcttctggg cacacgaccg ctttggtggc tacgctcaat ctggcctgtt ggctgaaatc  240
accccggaca aagcgttcca ggacaagctg tatccgttta cctgggatgc cgtacgttac  300
aacggcaagc tgattgctta cccgatcgct gttgaagcgt tatcgctgat ttataacaaa  360
gatctgctgc cgaacccgcc aaaaacctgg gaagagatcc cggcgctgga taaagaactg  420
aaagcgaaag gtaagagcgc gctgatgttc aacctgcaag aaccgtactt cacctggccg  480
ctgattgctg ctgacggggg ttatgcgttc aagtatgaaa acggcaagta cgacattaaa  540
gacgtgggcg tggataacgc tggcgcgaaa gcgggtctga ccttcctggt tgacctgatt  600
aaaaacaaac acatgaatgc agacaccgat tactccatcg cagaagctgc ctttaataaa  660
ggcgaaacag cgatgaccat caacggcccg tgggcatggt ccaacatcga caccagcaaa  720
gtgaattatg gtgtaacggt actgccgacc ttcaagggtc aaccatccaa accgttcgtt  780
ggcgtgctga gcgcaggtat taacgccgcc agtccgaaca aagagctggc aaaagagttc  840
ctcgaaaact atctgctgac tgatgaaggt ctggaagcgg ttaataaaga caaaccgctg  900
ggtgccgtag cgctgaagtc ttacgaggaa gagttggcga aagatccacg tattgccgcc  960
accatggaaa acgcccagaa aggtgaaatc atgccgaaca tcccgcagat gtccgctttc  1020
tggtatgccg tgcgtactgc ggtgatcaac gccgccagcg gtcgtcagac tgtcgatgaa  1080
gccctgaaag acgcgcagac taattcgggt accggtggtg gctccggtga tgacgacgac  1140
aagagtccca tgggtgaaga tatcccaacg accgaaaacc tgtattttca gggatccgaa  1200
ttc                                                                 1203

SEQ ID NO: 8           moltype = DNA  length = 294
FEATURE                Location/Qualifiers
misc_feature           1..294
                       note = SUMO1
source                 1..294
                       mol_type = other DNA
                       organism = synthetic construct
SEQUENCE: 8
atgtcggact cagaagtcaa tcaagaagct aagccagagg tcaagccaga agtcaagcct  60
gagactcaca tcaatttaaa ggtgtccgat ggatcttcag agatcttctt caagatcaaa  120
aagaccactc ctttaagaag gctgatggaa gcgttcgcta aaagacaggg taaggaaatg  180
gactccttaa gattcttgta cgacggtatt agaattcaag ctgatcagac ccctgaagat  240
ttggacatgg aggataacga tattattgag gctcacagag aacagattgg tggt         294

SEQ ID NO: 9           moltype = DNA  length = 306
FEATURE                Location/Qualifiers
misc_feature           1..306
                       note = SUMO2
source                 1..306
                       mol_type = other DNA
                       organism = synthetic construct
SEQUENCE: 9
atgggccatc atcatcacca tcacggcagc ctgcaagaag agaaaccgaa agagggcgtt  60
aagaccgaga atgaccacat taacctggtc gtcgctggtc aagatggcag cgtggtgcag  120
tttaagatca agcgtcacac gccgttgagc aagctgatga aggcttactg cgagcgtcag  180
ggtctgagca tgcgtcagat ccgctttcgt ttcgatggcc agccgatcaa tgagactgac  240
accccagcgc aactggagat ggaagatgaa gataccatcg acgtctttca gcaacagacc  300
ggtggt                                                              306

SEQ ID NO: 10          moltype = DNA  length = 567
FEATURE                Location/Qualifiers
misc_feature           1..567
                       note = TrxA
source                 1..567
```

```
                        mol_type = other DNA
                        organism = synthetic construct
SEQUENCE: 10
atgagcgata aaattattca cctgactgac gacagttttg acacggatgt actcaaagcg  60
gacggggcga tcctcgtcga tttctgggca gagtggtgcg gtccgtgcaa aatgatcgcc  120
ccgattctgg atgaaatcgc tgacgaatat cagggcaaac tgaccgttgc aaaactgaac  180
atcgatcaaa accctggcac tgcgccgaaa tatggcatcc gtggtatccc gactctgctg  240
ctgttcaaaa acggtgaagt ggcggcaacc aaagtgggtg cactgtctaa aggtcagttg  300
aaagagttcc tcgacgctaa cctggccggt tctggttctg gccatatgca ccatcatcat  360
catcattctt ctggtctggt gccacgcggt tctggtatga aagaaaccgc tgctgctaaa  420
ttcgaacgcc agcacatgga cagcccagat ctgggtaccg acgacgacga caaggccatg  480
ggttcccacc atcaccatca ccatcaccac ggttctgatt acgatatccc aacgaccgaa  540
aacctgtatt ttcagggatc cgaattc                                    567

SEQ ID NO: 11           moltype = DNA  length = 35
FEATURE                 Location/Qualifiers
misc_feature            1..35
                        note = primer GA001-P1-F4
source                  1..35
                        mol_type = other DNA
                        organism = synthetic construct
SEQUENCE: 11
tgccgaccgt ctagagtcga cctgcagaag cttag                           35

SEQ ID NO: 12           moltype = DNA  length = 45
FEATURE                 Location/Qualifiers
misc_feature            1..45
                        note = primer GA001-P1-R4
source                  1..45
                        mol_type = other DNA
                        organism = synthetic construct
SEQUENCE: 12
aactggcgtt acccaactta atcactagta ttatacctag gactg                45

SEQ ID NO: 13           moltype = DNA  length = 47
FEATURE                 Location/Qualifiers
misc_feature            1..47
                        note = primer GA001-P1-F1
source                  1..47
                        mol_type = other DNA
                        organism = synthetic construct
SEQUENCE: 13
tagtgattaa gttgggtaac gccagtttta gagctagaaa tagcaag              47

SEQ ID NO: 14           moltype = DNA  length = 35
FEATURE                 Location/Qualifiers
misc_feature            1..35
                        note = primer GA001-P1-R1
source                  1..35
                        mol_type = other DNA
                        organism = synthetic construct
SEQUENCE: 14
gttccggaat tcaaaaaaag caccgactcg gtgcc                           35

SEQ ID NO: 15           moltype = DNA  length = 39
FEATURE                 Location/Qualifiers
misc_feature            1..39
                        note = primer GA001-LF
source                  1..39
                        mol_type = other DNA
                        organism = synthetic construct
SEQUENCE: 15
gctttttttg aattccggaa cgggaaggcg actggagtg                       39

SEQ ID NO: 16           moltype = DNA  length = 37
FEATURE                 Location/Qualifiers
misc_feature            1..37
                        note = primer GA001-P1-LR
source                  1..37
                        mol_type = other DNA
                        organism = synthetic construct
SEQUENCE: 16
ggtgcgggcc tcgacggcca gtgaatccgt aatcatg                         37

SEQ ID NO: 17           moltype = DNA  length = 35
FEATURE                 Location/Qualifiers
misc_feature            1..35
                        note = primer GA001-P1-RR
source                  1..35
```

```
                        mol_type = other DNA
                        organism = synthetic construct
SEQUENCE: 17
tcgactctag acggtcggca aagaccagac cgttc                          35

SEQ ID NO: 18           moltype = DNA  length = 32
FEATURE                 Location/Qualifiers
misc_feature            1..32
                        note = primer GA001-P1-RF
source                  1..32
                        mol_type = other DNA
                        organism = synthetic construct
SEQUENCE: 18
ctggccgtcg aggcccgcac cgatcgccct tc                             32

SEQ ID NO: 19           moltype = DNA  length = 34
FEATURE                 Location/Qualifiers
misc_feature            1..34
                        note = primer nudK-f2
source                  1..34
                        mol_type = other DNA
                        organism = synthetic construct
SEQUENCE: 19
tgaattcttc ccttcctgaa tcatctgcaa aaac                           34

SEQ ID NO: 20           moltype = DNA  length = 34
FEATURE                 Location/Qualifiers
misc_feature            1..34
                        note = primer nudK-R2
source                  1..34
                        mol_type = other DNA
                        organism = synthetic construct
SEQUENCE: 20
gtggagtcgg taaaataaca ataatatttc gttg                           34

SEQ ID NO: 21           moltype = DNA  length = 36
FEATURE                 Location/Qualifiers
misc_feature            1..36
                        note = primer nudK-F3
source                  1..36
                        mol_type = other DNA
                        organism = synthetic construct
SEQUENCE: 21
attgttattt taccgactcc acagcgcgaa atgaac                         36

SEQ ID NO: 22           moltype = DNA  length = 29
FEATURE                 Location/Qualifiers
misc_feature            1..29
                        note = primer nudK-R3
source                  1..29
                        mol_type = other DNA
                        organism = synthetic construct
SEQUENCE: 22
ctagaccgga agagccgttt atcaatacc                                 29

SEQ ID NO: 23           moltype = DNA  length = 39
FEATURE                 Location/Qualifiers
misc_feature            1..39
                        note = primer nudK-F4
source                  1..39
                        mol_type = other DNA
                        organism = synthetic construct
SEQUENCE: 23
gataaacggc tcttccggtc tagagtcgac ctgcagaag                      39

SEQ ID NO: 24           moltype = DNA  length = 51
FEATURE                 Location/Qualifiers
misc_feature            1..51
                        note = primer nudK-R4
source                  1..51
                        mol_type = other DNA
                        organism = synthetic construct
SEQUENCE: 24
ctaaaacgcg cagctttcaa tcagctgact agtattatac ctaggactga g        51

SEQ ID NO: 25           moltype = DNA  length = 52
FEATURE                 Location/Qualifiers
misc_feature            1..52
                        note = primer nudK-F1
```

-continued

```
source                  1..52
                        mol_type = other DNA
                        organism = synthetic construct
SEQUENCE: 25
ctagtcagct gattgaaagc tgcgcgtttt agagctagaa atagcaagtt aa          52

SEQ ID NO: 26           moltype = DNA  length = 46
FEATURE                 Location/Qualifiers
misc_feature            1..46
                        note = primer nudK-R1
source                  1..46
                        mol_type = other DNA
                        organism = synthetic construct
SEQUENCE: 26
gattcaggaa gggaagaatt caaaaaaagc accgactcgg tgccac                 46

SEQ ID NO: 27           moltype = DNA  length = 39
FEATURE                 Location/Qualifiers
misc_feature            1..39
                        note = primer pT-nudD-F2
source                  1..39
                        mol_type = other DNA
                        organism = synthetic construct
SEQUENCE: 27
gcttttttg aattccactt cgtaatcctg aatatgcag                          39

SEQ ID NO: 28           moltype = DNA  length = 37
FEATURE                 Location/Qualifiers
misc_feature            1..37
                        note = primer pT-nudD-R2
source                  1..37
                        mol_type = other DNA
                        organism = synthetic construct
SEQUENCE: 28
cgctccactg attaccactg gctgacgccg gacgcac                           37

SEQ ID NO: 29           moltype = DNA  length = 43
FEATURE                 Location/Qualifiers
misc_feature            1..43
                        note = primer pT-nudD-F3
source                  1..43
                        mol_type = other DNA
                        organism = synthetic construct
SEQUENCE: 29
ccagtggtaa tcagtggagc gcactaccgt ggcaaagtct tcc                    43

SEQ ID NO: 30           moltype = DNA  length = 40
FEATURE                 Location/Qualifiers
misc_feature            1..40
                        note = primer pT-nudD-R3
source                  1..40
                        mol_type = other DNA
                        organism = synthetic construct
SEQUENCE: 30
cgactctaga gacaacttcc acccgagtaa ttcgcatgtg                        40

SEQ ID NO: 31           moltype = DNA  length = 48
FEATURE                 Location/Qualifiers
misc_feature            1..48
                        note = primer pT-nudD-F1
source                  1..48
                        mol_type = other DNA
                        organism = synthetic construct
SEQUENCE: 31
ctagtgtgag tggtgaaatc cgtgcgtttt agagctagaa atagcaag               48

SEQ ID NO: 32           moltype = DNA  length = 37
FEATURE                 Location/Qualifiers
misc_feature            1..37
                        note = primer pT-nudD-R1
source                  1..37
                        mol_type = other DNA
                        organism = synthetic construct
SEQUENCE: 32
gattacgaag tggaattcaa aaaaagcacc gactcgg                           37

SEQ ID NO: 33           moltype = DNA  length = 39
FEATURE                 Location/Qualifiers
misc_feature            1..39
```

```
                        note = primer pT-nudD-F4
source                  1..39
                        mol_type = other DNA
                        organism = synthetic construct
SEQUENCE: 33
ggtggaagtt gtctctagag tcgacctgca gaagcttag                         39

SEQ ID NO: 34           moltype = DNA  length = 52
FEATURE                 Location/Qualifiers
misc_feature            1..52
                        note = primer pT-nudD-R4
source                  1..52
                        mol_type = other DNA
                        organism = synthetic construct
SEQUENCE: 34
ctaaaacgca cggatttcac cactcacact agtattatac ctaggactga gc          52

SEQ ID NO: 35           moltype = DNA  length = 48
FEATURE                 Location/Qualifiers
misc_feature            1..48
                        note = primer WcaJ-F2
source                  1..48
                        mol_type = other DNA
                        organism = synthetic construct
SEQUENCE: 35
cgagtcggtg cttttttga attcgacagc ggcatgatcc cgtggctg                48

SEQ ID NO: 36           moltype = DNA  length = 36
FEATURE                 Location/Qualifiers
misc_feature            1..36
                        note = primer wacj-R2
source                  1..36
                        mol_type = other DNA
                        organism = synthetic construct
SEQUENCE: 36
cgccacgcca gcccaacagg tgcatgtaga ggaatg                            36

SEQ ID NO: 37           moltype = DNA  length = 37
FEATURE                 Location/Qualifiers
misc_feature            1..37
                        note = primer wcaJ-F3
source                  1..37
                        mol_type = other DNA
                        organism = synthetic construct
SEQUENCE: 37
catgcacctg ttgggctggc gtggcgaaac cgacacg                           37

SEQ ID NO: 38           moltype = DNA  length = 44
FEATURE                 Location/Qualifiers
misc_feature            1..44
                        note = primer wcaJ-R3
source                  1..44
                        mol_type = other DNA
                        organism = synthetic construct
SEQUENCE: 38
cagggtaata gatctaagct tgcgcggaac tgctgtccgt gggg                   44

SEQ ID NO: 39           moltype = DNA  length = 51
FEATURE                 Location/Qualifiers
misc_feature            1..51
                        note = primer wcaJ-F1
source                  1..51
                        mol_type = other DNA
                        organism = synthetic construct
SEQUENCE: 39
gtcctaggta taatactagt catcgccgca gcggtttcag gttttagagc t           51

SEQ ID NO: 40           moltype = DNA  length = 48
FEATURE                 Location/Qualifiers
misc_feature            1..48
                        note = primer wcaJ-R1
source                  1..48
                        mol_type = other DNA
                        organism = synthetic construct
SEQUENCE: 40
cagccacggg atcatgccgc tgtcgaattc aaaaaaagca ccgactcg               48

SEQ ID NO: 41           moltype = DNA  length = 44
FEATURE                 Location/Qualifiers
```

```
misc_feature           1..44
                       note = primer wcaJ-F4
source                 1..44
                       mol_type = other DNA
                       organism = synthetic construct
SEQUENCE: 41
ccccacggac agcagttccg cgcaagctta gatctattac cctg                  44

SEQ ID NO: 42          moltype = DNA  length = 45
FEATURE                Location/Qualifiers
misc_feature           1..45
                       note = primer wcaJ-R4
source                 1..45
                       mol_type = other DNA
                       organism = synthetic construct
SEQUENCE: 42
gctctaaaac ctgaaaccgc tgcggcgatg actagtatta tacct                 45

SEQ ID NO: 43          moltype = DNA  length = 29
FEATURE                Location/Qualifiers
misc_feature           1..29
                       note = primer LacZ-YZ1-F
source                 1..29
                       mol_type = other DNA
                       organism = synthetic construct
SEQUENCE: 43
cgcgctgtta gcgggcccat taagttctg                                   29

SEQ ID NO: 44          moltype = DNA  length = 28
FEATURE                Location/Qualifiers
misc_feature           1..28
                       note = primer LAC-YZ2-R
source                 1..28
                       mol_type = other DNA
                       organism = synthetic construct
SEQUENCE: 44
ggtcttcatc cacgcgcgcg tacatcgg                                    28

SEQ ID NO: 45          moltype = DNA  length = 24
FEATURE                Location/Qualifiers
misc_feature           1..24
                       note = primer wcaJ-YZ-for
source                 1..24
                       mol_type = other DNA
                       organism = synthetic construct
SEQUENCE: 45
gtcggcctgt tggcagaagc attc                                        24

SEQ ID NO: 46          moltype = DNA  length = 29
FEATURE                Location/Qualifiers
misc_feature           1..29
                       note = primer wcaJ-YZ-R
source                 1..29
                       mol_type = other DNA
                       organism = synthetic construct
SEQUENCE: 46
gtagccaaac agcagcgttc ttaccgcac                                   29

SEQ ID NO: 47          moltype = DNA  length = 23
FEATURE                Location/Qualifiers
misc_feature           1..23
                       note = primer nudD-YZ-F
source                 1..23
                       mol_type = other DNA
                       organism = synthetic construct
SEQUENCE: 47
ccgtcgccag ctgtgccact ttg                                         23

SEQ ID NO: 48          moltype = DNA  length = 26
FEATURE                Location/Qualifiers
misc_feature           1..26
                       note = primer nudD-YZ-R
source                 1..26
                       mol_type = other DNA
                       organism = synthetic construct
SEQUENCE: 48
caaactgtgc gaatcttaca atcgcc                                      26

SEQ ID NO: 49          moltype = DNA  length = 27
```

```
FEATURE                Location/Qualifiers
misc_feature           1..27
                       note = primer nudK-YZ-F
source                 1..27
                       mol_type = other DNA
                       organism = synthetic construct
SEQUENCE: 49
gctgagcatc aataaacaac aacgctg                                        27

SEQ ID NO: 50          moltype = DNA  length = 24
FEATURE                Location/Qualifiers
misc_feature           1..24
                       note = primer nudK-YZ-R
source                 1..24
                       mol_type = other DNA
                       organism = synthetic construct
SEQUENCE: 50
atgaagatgc gccgggcgtt tatg                                           24

SEQ ID NO: 51          moltype = DNA  length = 19
FEATURE                Location/Qualifiers
misc_feature           1..19
                       note = primer CX-targetF-F
source                 1..19
                       mol_type = other DNA
                       organism = synthetic construct
SEQUENCE: 51
cagcgagtca gtgagcgag                                                 19

SEQ ID NO: 52          moltype = DNA  length = 19
FEATURE                Location/Qualifiers
misc_feature           1..19
                       note = primer CX-targetF-R
source                 1..19
                       mol_type = other DNA
                       organism = synthetic construct
SEQUENCE: 52
gacattgcac tccaccgct                                                 19

SEQ ID NO: 53          moltype = DNA  length = 20
FEATURE                Location/Qualifiers
misc_feature           1..20
                       note = primer Kan-F
source                 1..20
                       mol_type = other DNA
                       organism = synthetic construct
SEQUENCE: 53
gaaggagaaa actcaccgag                                                20

SEQ ID NO: 54          moltype = DNA  length = 33
FEATURE                Location/Qualifiers
misc_feature           1..33
                       note = primer Pcr4-R1
source                 1..33
                       mol_type = other DNA
                       organism = synthetic construct
SEQUENCE: 54
cagctgcata aaattgcgat tggcaaaacc atc                                 33

SEQ ID NO: 55          moltype = DNA  length = 34
FEATURE                Location/Qualifiers
misc_feature           1..34
                       note = primer CBGW-manC-F
source                 1..34
                       mol_type = other DNA
                       organism = synthetic construct
SEQUENCE: 55
taaggagata taccatggcg cagtcgaaac tcta                                34

SEQ ID NO: 56          moltype = DNA  length = 45
FEATURE                Location/Qualifiers
misc_feature           1..45
                       note = primer CBGW-manC-R
source                 1..45
                       mol_type = other DNA
                       organism = synthetic construct
SEQUENCE: 56
gttaatttt tcatggtata tctcctttta cacccgtccg tagcg                     45
```

```
SEQ ID NO: 57          moltype = DNA  length = 51
FEATURE                Location/Qualifiers
misc_feature           1..51
                       note = primer CBGW-manB-F
source                 1..51
                       mol_type = other DNA
                       organism = synthetic construct
SEQUENCE: 57
cggacgggtg taaaaggaga tataccatga aaaaattaac ctgctttaaa g          51

SEQ ID NO: 58          moltype = DNA  length = 33
FEATURE                Location/Qualifiers
misc_feature           1..33
                       note = primer CBGW-manB-R
source                 1..33
                       mol_type = other DNA
                       organism = synthetic construct
SEQUENCE: 58
gagctcgaat tcttactcgt tcagcaacgt cag                              33

SEQ ID NO: 59          moltype = DNA  length = 34
FEATURE                Location/Qualifiers
misc_feature           1..34
                       note = primer CBGW-gmd-F
source                 1..34
                       mol_type = other DNA
                       organism = synthetic construct
SEQUENCE: 59
gaaggagata tacaatgtca aaagtcgctc tcat                             34

SEQ ID NO: 60          moltype = DNA  length = 46
FEATURE                Location/Qualifiers
misc_feature           1..46
                       note = primer CBGW-gmd-R
source                 1..46
                       mol_type = other DNA
                       organism = synthetic construct
SEQUENCE: 60
gttgtttact catggtatat ctccttttat gactccagcg cgatcg                46

SEQ ID NO: 61          moltype = DNA  length = 50
FEATURE                Location/Qualifiers
misc_feature           1..50
                       note = primer CBGW-wcaG-F
source                 1..50
                       mol_type = other DNA
                       organism = synthetic construct
SEQUENCE: 61
ctggagtcat aaaaggagat ataccatgag taaacaacga gtttttattg            50

SEQ ID NO: 62          moltype = DNA  length = 34
FEATURE                Location/Qualifiers
misc_feature           1..34
                       note = primer CBGW-wcaG-R
source                 1..34
                       mol_type = other DNA
                       organism = synthetic construct
SEQUENCE: 62
tggcagcagc ctaggttacc cccgaaagcg gtct                             34

SEQ ID NO: 63          moltype = DNA  length = 32
FEATURE                Location/Qualifiers
misc_feature           1..32
                       note = primer CBGW-F1
source                 1..32
                       mol_type = other DNA
                       organism = synthetic construct
SEQUENCE: 63
gctttcgggg gtaacctagg ctgctgccac cg                               32

SEQ ID NO: 64          moltype = DNA  length = 38
FEATURE                Location/Qualifiers
misc_feature           1..38
                       note = primer CBGW-R1
source                 1..38
                       mol_type = other DNA
                       organism = synthetic construct
SEQUENCE: 64
cgactgcgcc atggtatatc tccttattaa agttaaac                         38
```

-continued

```
SEQ ID NO: 65          moltype = DNA  length = 33
FEATURE                Location/Qualifiers
misc_feature           1..33
                       note = primer CBGW-F2
source                 1..33
                       mol_type = other DNA
                       organism = synthetic construct
SEQUENCE: 65
ttgctgaacg agtaagaatt cgagctcggc gcg                              33

SEQ ID NO: 66          moltype = DNA  length = 39
FEATURE                Location/Qualifiers
misc_feature           1..39
                       note = primer CBGW-R2
source                 1..39
                       mol_type = other DNA
                       organism = synthetic construct
SEQUENCE: 66
gcgacttttg acattgtata tctccttctt atacttaac                        39

SEQ ID NO: 67          moltype = DNA  length = 33
FEATURE                Location/Qualifiers
misc_feature           1..33
                       note = primer FL121-MBP-F
source                 1..33
                       mol_type = other DNA
                       organism = synthetic construct
SEQUENCE: 67
aaggagatat accatgaaaa tcgaagaagg taa                              33

SEQ ID NO: 68          moltype = DNA  length = 32
FEATURE                Location/Qualifiers
misc_feature           1..32
                       note = primer FL121-MBP-R
source                 1..32
                       mol_type = other DNA
                       organism = synthetic construct
SEQUENCE: 68
gatgctcata tggaattcgg atccctgaaa at                               32

SEQ ID NO: 69          moltype = DNA  length = 35
FEATURE                Location/Qualifiers
misc_feature           1..35
                       note = primer FL121-futC-F
source                 1..35
                       mol_type = other DNA
                       organism = synthetic construct
SEQUENCE: 69
cagggatccg aattccatat gagcatcatc cgtct                            35

SEQ ID NO: 70          moltype = DNA  length = 38
FEATURE                Location/Qualifiers
misc_feature           1..38
                       note = primer FL121-futC-R
source                 1..38
                       mol_type = other DNA
                       organism = synthetic construct
SEQUENCE: 70
gtgcggccgc aagcttagca gctgctgtgt ttatcaac                         38

SEQ ID NO: 71          moltype = DNA  length = 36
FEATURE                Location/Qualifiers
misc_feature           1..36
                       note = primer FL121-F
source                 1..36
                       mol_type = other DNA
                       organism = synthetic construct
SEQUENCE: 71
acagcagctg ctaagcttgc ggccgcactc gagcac                           36

SEQ ID NO: 72          moltype = DNA  length = 37
FEATURE                Location/Qualifiers
misc_feature           1..37
                       note = primer FL121-R
source                 1..37
                       mol_type = other DNA
                       organism = synthetic construct
SEQUENCE: 72
```

```
tcttcgattt tcatggtata tctccttctt aaagtta                       37

SEQ ID NO: 73           moltype = DNA  length = 33
FEATURE                 Location/Qualifiers
misc_feature            1..33
                        note = primer FL122-SUMO1-F
source                  1..33
                        mol_type = other DNA
                        organism = synthetic construct
SEQUENCE: 73
aaggagatat accatgtcgg actcagaagt caa                           33

SEQ ID NO: 74           moltype = DNA  length = 32
FEATURE                 Location/Qualifiers
misc_feature            1..32
                        note = primer FL122-SUMO1-R
source                  1..32
                        mol_type = other DNA
                        organism = synthetic construct
SEQUENCE: 74
gatgctcata tgaccaccaa tctgttctct gt                            32

SEQ ID NO: 75           moltype = DNA  length = 33
FEATURE                 Location/Qualifiers
misc_feature            1..33
                        note = primer FL122-futC-F
source                  1..33
                        mol_type = other DNA
                        organism = synthetic construct
SEQUENCE: 75
acagattggt ggtcatatga gcatcatccg tct                           33

SEQ ID NO: 76           moltype = DNA  length = 38
FEATURE                 Location/Qualifiers
misc_feature            1..38
                        note = primer FL122-futC-R
source                  1..38
                        mol_type = other DNA
                        organism = synthetic construct
SEQUENCE: 76
gtgcggccgc aagcttagca gctgctgtgt ttatcaac                      38

SEQ ID NO: 77           moltype = DNA  length = 34
FEATURE                 Location/Qualifiers
misc_feature            1..34
                        note = primer FL122-R
source                  1..34
                        mol_type = other DNA
                        organism = synthetic construct
SEQUENCE: 77
ctgagtccga catggtatat ctccttctta aagt                          34

SEQ ID NO: 78           moltype = DNA  length = 35
FEATURE                 Location/Qualifiers
misc_feature            1..35
                        note = primer FL123-SUMO2-F
source                  1..35
                        mol_type = other DNA
                        organism = synthetic construct
SEQUENCE: 78
ggaaggagat ataccatggg ccatcatcat cacca                         35

SEQ ID NO: 79           moltype = DNA  length = 32
FEATURE                 Location/Qualifiers
misc_feature            1..32
                        note = primer FL123-SUMO2-R
source                  1..32
                        mol_type = other DNA
                        organism = synthetic construct
SEQUENCE: 79
tgatgctcat atgaccaccg gtctgttgct ga                            32

SEQ ID NO: 80           moltype = DNA  length = 34
FEATURE                 Location/Qualifiers
misc_feature            1..34
                        note = primer FL123-futC-F
source                  1..34
                        mol_type = other DNA
                        organism = synthetic construct
```

```
SEQUENCE: 80
acagaccggt ggtcatatga gcatcatccg tctg                        34

SEQ ID NO: 81          moltype = DNA  length = 38
FEATURE                Location/Qualifiers
misc_feature           1..38
                       note = primer FL123-futC-R
source                 1..38
                       mol_type = other DNA
                       organism = synthetic construct
SEQUENCE: 81
gtgcggccgc aagcttagca gctgctgtgt ttatcaac                    38

SEQ ID NO: 82          moltype = DNA  length = 38
FEATURE                Location/Qualifiers
misc_feature           1..38
                       note = primer FL123-R
source                 1..38
                       mol_type = other DNA
                       organism = synthetic construct
SEQUENCE: 82
atgatgatgg cccatggtat atctccttct taaagtta                    38

SEQ ID NO: 83          moltype = DNA  length = 32
FEATURE                Location/Qualifiers
misc_feature           1..32
                       note = primer FL124-TrxA-F
source                 1..32
                       mol_type = other DNA
                       organism = synthetic construct
SEQUENCE: 83
aggagatata ccatgagcga taaaattatt ca                          32

SEQ ID NO: 84          moltype = DNA  length = 33
FEATURE                Location/Qualifiers
misc_feature           1..33
                       note = primer FL124-TrxA-R
source                 1..33
                       mol_type = other DNA
                       organism = synthetic construct
SEQUENCE: 84
tgatgctcat atggaattcg gatccctgaa aat                         33

SEQ ID NO: 85          moltype = DNA  length = 34
FEATURE                Location/Qualifiers
misc_feature           1..34
                       note = primer FL124-futC-F
source                 1..34
                       mol_type = other DNA
                       organism = synthetic construct
SEQUENCE: 85
agggatccga attccatatg agcatcatcc gtct                        34

SEQ ID NO: 86          moltype = DNA  length = 38
FEATURE                Location/Qualifiers
misc_feature           1..38
                       note = primer FL124-futC-R
source                 1..38
                       mol_type = other DNA
                       organism = synthetic construct
SEQUENCE: 86
gtgcggccgc aagcttagca gctgctgtgt ttatcaac                    38

SEQ ID NO: 87          moltype = DNA  length = 33
FEATURE                Location/Qualifiers
misc_feature           1..33
                       note = primer FL124-R
source                 1..33
                       mol_type = other DNA
                       organism = synthetic construct
SEQUENCE: 87
ttttatcgct catggtatat ctccttctta aag                         33

SEQ ID NO: 88          moltype = DNA  length = 37
FEATURE                Location/Qualifiers
misc_feature           1..37
                       note = primer FAB-futC-F
source                 1..37
                       mol_type = other DNA
```

```
                      organism = synthetic construct
SEQUENCE: 88
cgcgcggcag ccatcatatg agcatcatcc gtctgca                          37

SEQ ID NO: 89         moltype = DNA  length = 38
FEATURE               Location/Qualifiers
misc_feature          1..38
                      note = primer 28A-GT008-R
source                1..38
                      mol_type = other DNA
                      organism = synthetic construct
SEQUENCE: 89
gtgcggccgc aagcttagca gctgctgtgt ttatcaac                         38

SEQ ID NO: 90         moltype = DNA  length = 33
FEATURE               Location/Qualifiers
misc_feature          1..33
                      note = primer FAB-R1
source                1..33
                      mol_type = other DNA
                      organism = synthetic construct
SEQUENCE: 90
gatgatgctc atatgatggc tgccgcgcgg cac                              33

SEQ ID NO: 91         moltype = DNA  length = 1437
FEATURE               Location/Qualifiers
misc_feature          1..1437
                      note = manC gene
source                1..1437
                      mol_type = other DNA
                      organism = synthetic construct
SEQUENCE: 91
atggcgcagt cgaaactcta tccagttgtg atggcaggtg gctccggtag ccgcttatgg  60
ccgctttccc gcgtacttta ccccaagcag tttttatgcc tgaaaggcga tctcaccatg  120
ctgcaaacca ccatctgccg cctgaacggt gtggagtgcg aaagcccggt ggtgatttgc  180
aatgagcagc accgctttat tgtcgcggaa cagctgcgtc aactgaacaa actcaccaag  240
aacattattc tcgaaccggc agggcgtaac actgcacctg ccattgcgct ggcggcgctg  300
gcggcaaaac gtcatagccc ggagagcgac ccgttaatgc tggtcttggc ggcggatcat  360
gtgattgccg atgaagacgc gttccgtgcc gccgtgcgta atgccatgcc gtatgccaaa  420
gcgggcaagc tggtgacctt cggcattgtg ccggatctac ctgaaaccgg ttatggctat  480
attcgtcgcg gtgaagtgtc ggcgggtgag caggatacgg tggcctttga agtggcgcag  540
tttgtcgaaa aaccgaatct ggaaaccgct caggcctatg tggcaagcgg cgaatattac  600
tggaacagcg gtatgttcct gttccgcgcc ggacgctatc tcgaagaact gaaaaaatat  660
cgccccggata ttctcgatgc ctgtgaaaaa gcgatgagcg ccgtcgatcc ggatctcgat  720
tttattcgtg tggatgaaga agcgtttctc gcctgcccgg aagagtcggt ggattacgcg  780
gtcatggaac gtacggcaga tgccgttgtg gtgccgatgg atgcgggctg gagtgatgtc  840
ggttcttggt cttcattatg ggagatcagc gcccacaccg ccgagggcaa cgtttgccac  900
ggcgatgtga ttaatcacaa aactgaaaac agctatgtgt acgccgaatc tggcctggtc  960
accaccgtcg ggtgaaaga tttggtggta gtgcagacca aagatgcagt gctgattgcc  1020
gaccgtaacg cggtgcagga tgtgaaaaaa gtggtcgagc agatcaaagc cgatggtcgc  1080
catgagcatc gggtacatcg cgaagtgtat cgtccgtggg gcaaatatga ctctatcgac  1140
gcgggcgacc gctaccaggt gaaacgcatc accgtgaaac cgggcgaggg cttgtcggta  1200
cagatgcacc atcaccgcgc ggaacactgg gtagtggtcg cgggaacggc aaaagtcact  1260
attgacggtg atatcaaact gcttggtgaa aacgagtcca tttatattcc gctgggggcg  1320
acgcactgcc tggaaaaccc ggggaaaatt ccgctcgatt taattgaagt gcggtccggc  1380
tcttatctcg aagaggatga tgtggtgcgc ttcgcggatc gctacggacg ggtgtaa    1437

SEQ ID NO: 92         moltype = DNA  length = 1371
FEATURE               Location/Qualifiers
misc_feature          1..1371
                      note = manB gene
source                1..1371
                      mol_type = other DNA
                      organism = synthetic construct
SEQUENCE: 92
atgaaaaaat taacctgctt taaagcctat gatattcgtg gaaaattagg cgaagaactg  60
aatgaagata ttgcctggcg cattggtcgc gcttatggcg aatttctcaa accgaaaacc  120
attgtgttag gcggtgatgt ccgcctcacc agcgaaacct taaaactggc gctggcgaaa  180
ggtttacagg atgcgggcgt cgatgtgctg gatattggca tgtccggcac cgaagagatc  240
tatttcgcca cgttccatct cggtgtggat ggcggcattg aagttaccgc cagccataat  300
ccgatggatt ataacggcat gaagctggtg cgcgaagggg ctcgcccgat cagcggtgat  360
accggactgc gcgatgtcca gcgtctggca gaagccaacg actttcctcc cgttgatgaa  420
accaaacgcg gtcgctatca gcaaatcaat ctgcgtgacg cttacgttga tcacctgttc  480
ggttatatca acgtcaaaaa cctcacgccg ctcaagctgg tgatcaactc cgggaacggc  540
gcagcgggtc cggtggtgga cgctatcgaa gcccgcttta acgccctcgg cgctccggtg  600
gaattaatca aagtgcaaga cacgccggac ggcaatttcc ccaacggtat tcctaacccg  660
ctgctgccgg aatgccgcga cgacacccgc aatgcggtca tcaaacacgg cgcggatatg  720
ggcattgcct ttgacggtga ttttgatcgc tgtttcctgt ttgacgaaaa agggcagttt  780
atcgagggct actacattgt cggcctgttg gcagaagcat tcctcgaaaa aaatcccggc  840
```

```
gcgaagatca tccacgatcc acgtctctcc tggaacaccg ttgatgtggt gactaccgca  900
ggtggcaccc cggtaatgtc gaaaaccgga cacgccttta ttaaagaacg tatgcgcaag  960
gaagacgcca tctacggtgg cgaaatgagc gcccaccatt acttccgtga tttcgcttac  1020
tgcgacagcg gcatgatccc gtggctgctg gtcgccgaac tggtgtgcct gaaagagaaa  1080
acgctgggcg aactggtacg cgaccggatg gcggcgtttc cggcaagcgg tgagatcaac  1140
agcaaactgg cgcaacccgt tgaggcgatt aaccgcgtcg aacagcattt tagccgcgag  1200
gcgctggcgg tggatcgcac tgatggcatc agcatgacct ttgccgactg gcgctttaac  1260
ctgcgcacct ccaataccga accggtggtg cgcctgaatg tggaatcgcg cggtgatgtg  1320
ccgctgatgg aagcgcgaac gcgaactctg ctgacgttgc tgaacgagta a           1371
```

```
SEQ ID NO: 93          moltype = DNA  length = 1122
FEATURE                Location/Qualifiers
misc_feature           1..1122
                       note = gmd gene
source                 1..1122
                       mol_type = other DNA
                       organism = synthetic construct
SEQUENCE: 93
atgtcaaaag tcgctctcat caccggtgta accggacaag acggttctta cctggcagag  60
tttctgctgg aaaaaggtta cgaggtgcat ggtattaagc gtcgtgcatc gtcattcaac  120
accgagcgcg tggatcacat ttatcaggat ccgcacacct gcaacccgaa attccatctg  180
cattatggcg acctgagtga tacctccaac ctgacacgca ttttgcgtga agtgcagccg  240
gatgaagtgt ataacctggg cgcaatgagc cacgttgcgg tctcttttga gtcaccggaa  300
tataccgcag acgttgatgc gatgggtacg ctgcgcctgc tcgaggcgat ccgcttcctc  360
ggtctggaaa agaaaacccg tttttatcag gcttccacct ctgaactgta cggtctggtg  420
caggaaattc cgcagaaaga aactacgccg ttctacccgc gatctccgta tgcggtcgcc  480
aaactgtacg cctactggat caccgttaac taccgcgaat cctacggcat gtacgcctgt  540
aacggtattc tcttcaacca tgaatccccg cgccgcggtg aaaccttcgt tacccgcaaa  600
atcacccgcg caatcgccaa tatcgcccag gggctggagt cgtgcctgta cctcggcaat  660
atggattccc tgcgtgactg gggccatgcc aaagactacg taaaaatgca gtggatgatg  720
ctgcaacagg aacagccgga agatttcgtt attgctaccg gcgttcagta ctccgtacgt  780
cagttcgtgg aaatggcggc agcacagttg ggcatcaaac tgcgctttga aggcacgggt  840
gttgaagaga agggcattgt ggtttccgtc accgggcatg acgcgccggg cgttaaaccg  900
ggtgatgtga ttatcgccgt tgacccgcgt tacttccgtc cggcagaagt tgaaacgctg  960
ctcggcgacc cgaccaaagc gcacgaaaaa ctgggctgga aaccggaaat caccctcaga  1020
gagatggtgt ctgaaatggt ggctaatgac ctcgaagcgg cgaaaaaaca ctctctgctg  1080
aaatctcacg gctacgacgt ggcgatcgcg ctggagtcat aa                    1122
```

```
SEQ ID NO: 94          moltype = DNA  length = 965
FEATURE                Location/Qualifiers
misc_feature           1..965
                       note = wcaG gene
source                 1..965
                       mol_type = other DNA
                       organism = synthetic construct
SEQUENCE: 94
atgagtaaac aacgagtttt tattgctggt catcgcggga tggtcggttc tgccatcagg  60
cggcagctcg aacagcgcgg tgatgtggaa ctggtattac gcacccgcga cgagctgaac  120
ctgttggaca gccgcgcggt gcatgatttc tttgccagcg aacgcattga ccaggtctat  180
ctggcggcgg cgaaagtggg cggcattgtt gctaacaaca cctatccggc ggatttcatc  240
taccagaaca tgatgattga gagcaacatc attcacgccg cgcatcagaa cgacgtgaac  300
aaactgctgt ttctcggatc gtcctgtatc tacccgaaac tggcaaaaca gccgatggca  360
gaaagcgagt tgttgcaggg cacgctggag ccgactaacg agccttatgc tattgccaaa  420
atcgccggga tcaaactgtg cgaatcttac aatcgccagt acggacgaga ttaccgttca  480
gtcatgccga ccaacctgta cgggccgcac gacaacttcc acccgagtaa ttcgcatgtg  540
atcccagcat tgctgcgccg cttccacgag gcgacggcac agaatgcacc ggacgtggtg  600
gtatggggca gcggtacacc gatgcgtgaa ttcctgcacg tcgatgatat ggcggcggcg  660
agcattcatg tcatggagct ggcgcatgaa gtctggctgg agaacaccca gccgatgctg  720
tcgcacatta acgtcggcac gggcgttgac tgcaccatcc gtgaactggc gcaaaccatc  780
gccaaagtgg tgggttacaa aggtcgggtg gtttttgatg ccagcaaacc ggatggtacg  840
ccgcgcaaac tgctggatgt gacgcgcctg catcagcttg gctggtatca cgaaatctca  900
ctggaagcgg ggcttgccag cacttaccag tggttccttg agaatcaaga ccgctttcgg  960
gggta                                                             965
```

```
SEQ ID NO: 95          moltype = AA  length = 478
FEATURE                Location/Qualifiers
REGION                 1..478
                       note = manC protein
source                 1..478
                       mol_type = protein
                       organism = synthetic construct
SEQUENCE: 95
MAQSKLYPVV MAGGSGSRLW PLSRVLYPKQ FLCLKGDLTM LQTTICRLNG VECESPVVIC  60
NEQHRFIVAE QLRQLNKLTK NIILEPAGRN TAPAIALAAL AAKRHSPESD PLMLVLAADH  120
VIADEDAFRA AVRNAMPYAK AGKLVTFGIV PDLPETGYGY IRRGEVSAGE QDTVAFEVAQ  180
FVEKPNLETA QAYVASGEYY WNSGMFLFRA GRYLEELKKY RPDILDACEK AMSAVDPDLD  240
FIRVDEEAFL ACPEESVDYA VMERTADAVV VPMDAGWSDV GSWSSLWEIS AHTAEGNVCH  300
GDVINHKTEN SYVYAESGLV TTVGVKDLVV VQTKDAVLIA DRNAVQDVKK VVEQIKADGR  360
HEHRVHREVY RPWGKYDSID AGDRYQVKRI TVKPGEGLSV QMHHHRAEHW VVVAGTAKVT  420
```

-continued

```
IDGDIKLLGE NESIYIPLGA THCLENPGKI PLDLIEVRSG SYLEEDDVVR FADRYGRV    478

SEQ ID NO: 96          moltype = AA  length = 456
FEATURE                Location/Qualifiers
REGION                 1..456
                       note = manB protein
source                 1..456
                       mol_type = protein
                       organism = synthetic construct
SEQUENCE: 96
MKKLTCFKAY DIRGKLGEEL NEDIAWRIGR AYGEFLKPKT IVLGGDVRLT SETLKLALAK  60
GLQDAGVDVL DIGMSGTEEI YFATFHLGVD GGIEVTASHN PMDYNGMKLV REGARPISGD  120
TGLRDVQRLA EANDFPPVDE TKRGRYQQIN LRDAYVDHLF GYINVKNLTP LKLVINSGNG  180
AAGPVVDAIE ARFNALGAPV ELIKVHNTPD GNFPNGIPNP LLPECRDDTR NAVIKHGADM  240
GIAFDGDFDR CFLFDEKGQF IEGYYIVGLL AEAFLEKNPG AKIIHDPRLS WNTVDVVTTA  300
GGTPVMSKTG HAFIKERMRK EDAIYGGEMS AHHYFRDFAY CDSGMIPWLL VAELVCLKEK  360
TLGELVRDRM AAFPASGEIN SKLAQPVEAI NRVEQHFSRE ALAVDRTDGI SMTFADWRFN  420
LRTSNTEPVV RLNVESRGDV PLMEARTRTL LTLLNE                            456

SEQ ID NO: 97          moltype = AA  length = 373
FEATURE                Location/Qualifiers
REGION                 1..373
                       note = gmd protein
source                 1..373
                       mol_type = protein
                       organism = synthetic construct
SEQUENCE: 97
MSKVALITGV TGQDGSYLAE FLLEKGYEVH GIKRRASSFN TERVDHIYQD PHTCNPKFHL  60
HYGDLSDTSN LTRILREVQP DEVYNLGAMS HVAVSFESPE YTADVDAMGT LRLLEAIRFL  120
GLEKKTRFYQ ASTSELYGLV QEIPQKETTP FYPRSPYAVA KLYAYWITVN YRESYGMYAC  180
NGILFNHESP RRGETFVTRK ITRAIANIAQ GLESCLYLGN MDSLRDWGHA KDYVKMQWMM  240
LQQEQPEDFV IATGVQYSVR QFVEMAAAQL GIKLRFEGTG VEEKGIVVSV TGHDAPGVKP  300
GDVIIAVDPR YFRPAEVETL LGDPTKAHEK LGWKPEITLR EMVSEMVAND LEAAKKHSLL  360
KSHGYDVAIA LES                                                     373

SEQ ID NO: 98          moltype = AA  length = 321
FEATURE                Location/Qualifiers
REGION                 1..321
                       note = wcaG protein
source                 1..321
                       mol_type = protein
                       organism = synthetic construct
SEQUENCE: 98
MSKQRVFIAG HRGMVGSAIR RQLEQRGDVE LVLRTRDELN LLDSRAVHDF FASERIDQVY  60
LAAAKVGGIV ANNTYPADFI YQNMMIESNI IHAAHQNDVN KLLFLGSSCI YPKLAKQPMA  120
ESELLQGTLE PTNEPYAIAK IAGIKLCESY NRQYGRDYRS VMPTNLYGPH DNFHPSNSHV  180
IPALLRRFHE ATAQNAPDVV VWGSGTPMRE FLHVDDMAAA SIHVMELAHE VWLENTQPML  240
SHINVGTGVD CTIRELAQTI AKVVGYKGRV VFDASKPDGT PRKLLDVTRL HQLGWYHEIS  300
LEAGLASTYQ WFLENQDRFR G                                            321
```